US008957268B2

(12) United States Patent
Cohen et al.

(10) Patent No.: US 8,957,268 B2
(45) Date of Patent: Feb. 17, 2015

(54) METHODS OF REFINING NATURAL OIL FEEDSTOCKS

(75) Inventors: Steven A. Cohen, Naperville, IL (US); Melvin L. Luetkens, Jr., Batavia, IL (US); Chander Balakrishnan, Oak Park, IL (US); Robert Snyder, Naperville, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 394 days.

(21) Appl. No.: 12/901,829

(22) Filed: Oct. 11, 2010

(65) Prior Publication Data
US 2011/0113679 A1 May 19, 2011

Related U.S. Application Data

(60) Provisional application No. 61/250,743, filed on Oct. 12, 2009.

(51) Int. Cl.
*C11C 1/00* (2006.01)
*C07C 1/00* (2006.01)
(Continued)

(52) U.S. Cl.
CPC . *C11B 3/00* (2013.01); *C10G 45/00* (2013.01); *C10G 45/58* (2013.01); *C10G 50/00* (2013.01); *C10G 65/043* (2013.01); *C10L 1/026* (2013.01); *C10L 1/08* (2013.01); *C11C 3/003* (2013.01); *C10G 3/42* (2013.01); *C10G 2300/30* (2013.01); *C10G 2300/301* (2013.01);
(Continued)

(58) Field of Classification Search
USPC ............ 554/170; 585/14, 240, 250, 310, 324, 585/638, 639, 640
See application file for complete search history.

(56) References Cited

U.S. PATENT DOCUMENTS 2,190,593 A    2/1940  Clayton
2,484,841 A *  10/1949 Lorand ......................... 568/814
(Continued)

FOREIGN PATENT DOCUMENTS

DE    102005010345 B3    6/2006
EP    0 116 408 A2       8/1984
(Continued)

OTHER PUBLICATIONS

Sakamuri, "Esters" in Kirk-Othmer Encyclopedia of Chemical Technology, John Wiley & Sons, 2001, available on-line Dec. 19, 2003.*
(Continued)

*Primary Examiner* — Thuan D Dang
(74) *Attorney, Agent, or Firm* — Robert S. Dailey

(57) ABSTRACT

Methods are provided for refining natural oil feedstocks. The methods comprise reacting the feedstock in the presence of a metathesis catalyst under conditions sufficient to form a metathesized product comprising olefins and esters. In certain embodiments, the methods further comprise separating the olefins from the esters in the metathesized product. In certain embodiments, the methods further comprise hydrogenating the olefins under conditions sufficient to form a fuel composition. In certain embodiments, the methods further comprise transesterifying the esters in the presence of an alcohol to form a transesterified product.

27 Claims, 2 Drawing Sheets

(51) Int. Cl.

| | | |
|---|---|---|
| *C07C 5/03* | (2006.01) | |
| *C07C 1/24* | (2006.01) | |
| *C11B 3/00* | (2006.01) | |
| *C10G 45/00* | (2006.01) | |
| *C10G 45/58* | (2006.01) | |
| *C10G 50/00* | (2006.01) | |
| *C10G 65/04* | (2006.01) | |
| *C10L 1/02* | (2006.01) | |
| *C10L 1/08* | (2006.01) | |
| *C11C 3/00* | (2006.01) | |
| *C10G 3/00* | (2006.01) | |
| *C07C 67/03* | (2006.01) | |
| *C07C 67/54* | (2006.01) | |
| *C07C 6/04* | (2006.01) | |
| *C07C 51/09* | (2006.01) | |
| *C07C 2/86* | (2006.01) | |

(52) U.S. Cl.
CPC ... *C10G 2300/307* (2013.01); *C10G 2300/308* (2013.01); *C10G 2300/44* (2013.01); *C10G 2400/02* (2013.01); *C10G 2400/04* (2013.01); *C10G 2400/08* (2013.01); *C10G 2400/20* (2013.01); *C10G 2400/22* (2013.01); *C10G 2300/1014* (2013.01); *C10G 2300/1018* (2013.01); *C10G 2300/1092* (2013.01); *C10G 2300/1096* (2013.01); *Y02E 50/13* (2013.01); *Y02T 50/678* (2013.01); *C07C 67/03* (2013.01); *C07C 67/54* (2013.01); *C07C 6/04* (2013.01); *C07C 51/09* (2013.01); *C07C 2/862* (2013.01); *C07C 2531/14* (2013.01); *C07C 2531/24* (2013.01)
USPC ............. 585/310; 585/14; 585/240; 585/250; 585/324; 585/638; 585/639; 585/640; 554/170

(56) References Cited

U.S. PATENT DOCUMENTS

| | | | |
|---|---|---|---|
| 3,150,205 A | 9/1964 | Krane et al. | |
| 3,351,566 A | 11/1967 | Taylor et al. | |
| 3,507,890 A * | 4/1970 | Dieckelmann et al. | 560/127 |
| 4,210,771 A | 7/1980 | Holcombe | |
| 4,465,890 A | 8/1984 | Kukes et al. | |
| 4,554,065 A * | 11/1985 | Albinson et al. | 208/59 |
| 4,579,991 A | 4/1986 | White | |
| 4,613,410 A * | 9/1986 | Rivers, Jr. | 203/39 |
| 4,943,396 A | 7/1990 | Johnson | |
| 4,992,605 A | 2/1991 | Craig et al. | |
| 5,043,485 A | 8/1991 | Fleckenstein et al. | |
| 5,091,116 A | 2/1992 | Krishnamurthy et al. | |
| 5,095,169 A | 3/1992 | Skeels et al. | |
| 5,113,030 A | 5/1992 | Chen et al. | |
| 5,120,896 A | 6/1992 | Kemp et al. | |
| 5,146,033 A | 9/1992 | Schrock et al. | |
| 5,191,145 A | 3/1993 | Allen et al. | |
| 5,262,076 A | 11/1993 | Ishida et al. | |
| 5,264,606 A | 11/1993 | Moloy et al. | |
| 5,298,271 A | 3/1994 | Takashina et al. | |
| 5,298,638 A | 3/1994 | Toeneboehn et al. | |
| 5,342,909 A | 8/1994 | Grubbs et al. | |
| 5,348,755 A | 9/1994 | Roy | |
| 5,374,751 A | 12/1994 | Cheng et al. | |
| 5,391,385 A | 2/1995 | Seybold | |
| 5,399,731 A * | 3/1995 | Wimmer | 554/167 |
| 5,401,866 A | 3/1995 | Cheng et al. | |
| 5,414,184 A | 5/1995 | Wu et al. | |
| 5,432,083 A | 7/1995 | Copeland et al. | |
| 5,484,201 A | 1/1996 | Goolsbee | |
| 5,532,163 A | 7/1996 | Yagi et al. | |
| 5,560,950 A | 10/1996 | Conte et al. | |
| 5,596,111 A | 1/1997 | Sibi et al. | |
| 5,597,600 A | 1/1997 | Munson et al. | |
| 5,653,966 A | 8/1997 | Bertoli et al. | |
| 5,672,802 A | 9/1997 | Lutz | |
| 5,675,051 A | 10/1997 | Chauvin et al. | |
| 5,747,409 A | 5/1998 | Commereuc | |
| 5,824,354 A | 10/1998 | Ritter et al. | |
| 5,840,942 A | 11/1998 | Oude Alink | |
| 5,864,049 A | 1/1999 | Dos Santos et al. | |
| 5,880,298 A | 3/1999 | Hillion et al. | |
| 5,883,272 A | 3/1999 | Noweck et al. | |
| 5,932,261 A | 8/1999 | Unnithan | |
| 5,939,572 A | 8/1999 | Sibi et al. | |
| 5,959,129 A | 9/1999 | van Dam et al. | |
| 5,972,057 A | 10/1999 | Hayafuji et al. | |
| 6,033,706 A | 3/2000 | Silkeberg et al. | |
| 6,075,158 A | 6/2000 | Hill | |
| 6,127,560 A | 10/2000 | Stidham et al. | |
| 6,127,561 A | 10/2000 | Jeromin et al. | |
| 6,129,945 A | 10/2000 | Awad et al. | |
| 6,162,480 A | 12/2000 | van Buuren et al. | |
| 6,166,279 A | 12/2000 | Schwab et al. | |
| 6,172,248 B1 | 1/2001 | Copeland et al. | |
| 6,175,047 B1 | 1/2001 | Hori et al. | |
| 6,207,209 B1 | 3/2001 | Jirjis et al. | |
| 6,210,732 B1 | 4/2001 | Papanton | |
| 6,214,764 B1 | 4/2001 | Gillespie | |
| 6,215,019 B1 | 4/2001 | Pederson et al. | |
| 6,248,911 B1 | 6/2001 | Canessa et al. | |
| 6,251,460 B1 | 6/2001 | Ganguli et al. | |
| 6,265,495 B1 | 7/2001 | Hirata et al. | |
| 6,271,430 B2 | 8/2001 | Schwab et al. | |
| 6,284,852 B1 | 9/2001 | Lynn et al. | |
| 6,288,251 B1 | 9/2001 | Tsuto et al. | |
| 6,303,837 B1 | 10/2001 | Gürtler et al. | |
| 6,313,365 B1 | 11/2001 | Hori et al. | |
| 6,368,648 B1 | 4/2002 | Bertram et al. | |
| 6,376,581 B1 | 4/2002 | Tanaka et al. | |
| 6,388,038 B1 | 5/2002 | Hirata et al. | |
| 6,395,669 B1 | 5/2002 | Sartain et al. | |
| 6,409,778 B1 | 6/2002 | Auschra et al. | |
| 6,440,057 B1 | 8/2002 | Ergün et al. | |
| 6,492,564 B1 | 12/2002 | Wiese et al. | |
| 6,506,944 B1 | 1/2003 | Schwab et al. | |
| 6,552,139 B1 | 4/2003 | Herrmann et al. | |
| 6,552,208 B1 | 4/2003 | Alander et al. | |
| 6,583,236 B1 | 6/2003 | Giardello et al. | |
| 6,605,748 B2 | 8/2003 | Wagener et al. | |
| 6,638,551 B1 | 10/2003 | Levy et al. | |
| 6,646,172 B1 | 11/2003 | Schwab et al. | |
| 6,677,495 B1 | 1/2004 | Schwab et al. | |
| 6,696,597 B2 | 2/2004 | Pederson et al. | |
| 6,706,299 B2 | 3/2004 | Thengumpillil et al. | |
| 6,740,134 B2 | 5/2004 | Angelico et al. | |
| 6,758,869 B2 | 7/2004 | Roeske et al. | |
| 6,761,869 B1 | 7/2004 | Virtanen | |
| 6,800,316 B1 | 10/2004 | Perrut et al. | |
| 6,833,149 B2 | 12/2004 | Jirjis et al. | |
| 6,846,772 B2 | 1/2005 | Lok et al. | |
| 6,852,900 B2 | 2/2005 | Wurziger et al. | |
| 6,900,347 B2 | 5/2005 | Paulson et al. | |
| 6,916,448 B2 | 7/2005 | Commereuc et al. | |
| 6,960,272 B1 | 11/2005 | Tokas et al. | |
| 6,962,729 B2 | 11/2005 | Tokas et al. | |
| 6,982,155 B1 | 1/2006 | Fukuda et al. | |
| 6,998,050 B2 | 2/2006 | Nakajoh et al. | |
| 7,025,851 B2 | 4/2006 | Caster et al. | |
| 7,026,495 B1 | 4/2006 | Pederson et al. | |
| 7,045,100 B2 | 5/2006 | Ergün et al. | |
| 7,045,114 B2 | 5/2006 | Tonkovich et al. | |
| 7,060,316 B2 | 6/2006 | Sakai et al. | |
| 7,067,584 B2 | 6/2006 | Rink et al. | |
| 7,119,216 B2 | 10/2006 | Newman et al. | |
| 7,141,083 B2 | 11/2006 | Jordan | |
| 7,144,433 B2 | 12/2006 | Jordan | |
| 7,144,435 B2 | 12/2006 | Jordan | |
| 7,160,338 B2 | 1/2007 | Jordan | |
| 7,160,339 B2 | 1/2007 | Jordan | |
| 7,176,336 B2 | 2/2007 | Maughon et al. | |
| 7,220,289 B2 | 5/2007 | Jordan | |
| 7,276,616 B2 | 10/2007 | Dwyer et al. | |

(56) References Cited

U.S. PATENT DOCUMENTS

| | | |
|---|---|---|
| 7,320,809 B2 | 1/2008 | Friedman et al. |
| 7,361,621 B2 | 4/2008 | Yang et al. |
| 7,431,749 B2 | 10/2008 | Kim et al. |
| 7,442,248 B2 | 10/2008 | Timmons |
| 7,449,591 B2 | 11/2008 | Brenner et al. |
| 7,452,515 B1 | 11/2008 | Lafleur et al. |
| 7,507,846 B2 | 3/2009 | Pelly |
| 7,507,854 B2 | 3/2009 | Lee et al. |
| 7,511,101 B2 | 3/2009 | Nguyen et al. |
| 7,553,982 B1 | 6/2009 | Morris |
| 7,563,915 B2 | 7/2009 | Matson et al. |
| 7,576,227 B2 | 8/2009 | Lysenko et al. |
| 7,585,990 B2 | 9/2009 | van Toor et al. |
| 7,597,783 B2 | 10/2009 | Kruidenberg |
| 7,598,407 B2 | 10/2009 | Kruidenberg |
| 7,601,309 B2 | 10/2009 | Krupa et al. |
| 7,612,221 B2 | 11/2009 | Haas et al. |
| 7,626,047 B2 | 12/2009 | Nakayama et al. |
| 7,626,048 B2 | 12/2009 | Soane et al. |
| 7,645,807 B1 | 1/2010 | Goetsch et al. |
| 7,652,145 B2 | 1/2010 | Herrmann et al. |
| 7,652,156 B2 | 1/2010 | Hillion et al. |
| 7,666,234 B2 | 2/2010 | Ghosh et al. |
| 7,671,224 B2 | 3/2010 | Winde et al. |
| 7,695,533 B2 | 4/2010 | Kovacs et al. |
| 7,696,376 B2 | 4/2010 | Furuta |
| 7,696,398 B2 | 4/2010 | Burdett et al. |
| 7,718,833 B2 | 5/2010 | Potthast et al. |
| 7,737,233 B2 | 6/2010 | Obrecht et al. |
| 7,743,828 B2 | 6/2010 | Roddy et al. |
| 7,745,652 B2 | 6/2010 | Lysenko et al. |
| 7,750,172 B2 | 7/2010 | Grubbs et al. |
| 7,790,651 B2 | 9/2010 | Lin et al. |
| 7,806,945 B2 | 10/2010 | Jackam et al. |
| 7,812,185 B2 | 10/2010 | Burdett et al. |
| 7,812,187 B2 | 10/2010 | Kawashima et al. |
| 7,838,711 B2 | 11/2010 | Herweck et al. |
| 7,846,995 B2 | 12/2010 | Ong et al. |
| 7,858,710 B2 | 12/2010 | Wagener et al. |
| 7,863,471 B2 | 1/2011 | Krause et al. |
| 7,875,736 B2 | 1/2011 | Wang et al. |
| 7,902,417 B2 | 3/2011 | Goldman et al. |
| 7,905,288 B2 | 3/2011 | Kinkead |
| 7,906,665 B2 | 3/2011 | Lin et al. |
| 7,939,688 B2 | 5/2011 | Meudt et al. |
| 7,951,967 B2 | 5/2011 | Chun et al. |
| 7,960,598 B2 | 6/2011 | Spilker et al. |
| 8,039,652 B2 | 10/2011 | Portnoff et al. |
| 8,039,653 B2 | 10/2011 | Soane et al. |
| 8,044,149 B2 | 10/2011 | Iwasaki et al. |
| 8,066,954 B2 | 11/2011 | Nguyen et al. |
| 8,071,799 B2 | 12/2011 | Olson |
| 8,147,766 B2 | 4/2012 | Spilker et al. |
| 8,148,477 B2 | 4/2012 | Saita et al. |
| 8,163,946 B2 | 4/2012 | Yan et al. |
| 8,192,696 B2 | 6/2012 | Gurski et al. |
| 8,207,362 B2 | 6/2012 | Morris |
| 8,227,371 B2 | 7/2012 | Holtcamp et al. |
| 8,227,635 B2 | 7/2012 | Bowden et al. |
| 8,237,003 B2 | 8/2012 | Holtcamp et al. |
| 8,293,181 B2 | 10/2012 | Saita et al. |
| 8,309,055 B2 | 11/2012 | Arstad et al. |
| 8,324,334 B2 | 12/2012 | Jones et al. |
| 8,324,413 B2 | 12/2012 | O'Rear |
| 8,334,396 B2 | 12/2012 | Papadogianakis et al. |
| 2003/0055184 A1* | 3/2003 | Song et al. .................... 526/160 |
| 2003/0135080 A1 | 7/2003 | Botha et al. |
| 2003/0236175 A1 | 12/2003 | Twu et al. |
| 2005/0070750 A1* | 3/2005 | Newman et al. ............. 585/643 |
| 2005/0154221 A1* | 7/2005 | Lysenko et al. ............. 554/174 |
| 2005/0203324 A1 | 9/2005 | Lee et al. |
| 2006/0042158 A1 | 3/2006 | Lee |
| 2006/0047176 A1 | 3/2006 | Gartside et al. |
| 2006/0069274 A1 | 3/2006 | Dias De Moraes E. Silva et al. |
| 2006/0167326 A1 | 7/2006 | Burdett et al. |
| 2007/0011943 A1 | 1/2007 | Lin |
| 2007/0151146 A1 | 7/2007 | Lee et al. |
| 2007/0179302 A1 | 8/2007 | Olivier-Bourbigou et al. |
| 2007/0208206 A1 | 9/2007 | Obrecht et al. |
| 2007/0217965 A1 | 9/2007 | Johnson et al. |
| 2007/0225536 A1 | 9/2007 | Lutz |
| 2007/0227400 A1 | 10/2007 | Zullo et al. |
| 2007/0277430 A1 | 12/2007 | Jackman et al. |
| 2008/0027194 A1 | 1/2008 | Schrodi |
| 2008/0047194 A1 | 2/2008 | Prawoto |
| 2008/0097114 A1 | 4/2008 | Bakshi |
| 2008/0103346 A1 | 5/2008 | Burdett et al. |
| 2008/0115407 A1 | 5/2008 | Hoffman |
| 2008/0119664 A1 | 5/2008 | Sinoncelli et al. |
| 2008/0202021 A1 | 8/2008 | Powell |
| 2008/0228017 A1 | 9/2008 | Burdett et al. |
| 2008/0229654 A1* | 9/2008 | Bradin ......................... 44/308 |
| 2008/0244962 A1 | 10/2008 | Abhari et al. |
| 2008/0282606 A1 | 11/2008 | Plaza et al. |
| 2008/0300434 A1 | 12/2008 | Cortright et al. |
| 2008/0306230 A1 | 12/2008 | Pan et al. |
| 2009/0038209 A1 | 2/2009 | Farid et al. |
| 2009/0048459 A1 | 2/2009 | Tupy et al. |
| 2009/0069516 A1 | 3/2009 | Obrecht et al. |
| 2009/0112007 A1 | 4/2009 | Lin et al. |
| 2009/0143544 A1 | 6/2009 | Lysenko et al. |
| 2009/0145022 A1 | 6/2009 | Ng et al. |
| 2009/0163731 A1 | 6/2009 | Martin et al. |
| 2009/0165366 A1 | 7/2009 | Jovanovic et al. |
| 2009/0178330 A1 | 7/2009 | Lebron Parejo et al. |
| 2009/0183420 A1 | 7/2009 | Cobb |
| 2009/0203860 A1 | 8/2009 | Bergbreiter et al. |
| 2009/0264672 A1 | 10/2009 | Abraham et al. |
| 2009/0287004 A1 | 11/2009 | Bergman et al. |
| 2009/0306441 A1 | 12/2009 | Basset et al. |
| 2009/0307966 A1 | 12/2009 | Yan et al. |
| 2009/0324514 A1 | 12/2009 | Awad |
| 2009/0326295 A1 | 12/2009 | Krupa et al. |
| 2010/0010246 A1 | 1/2010 | Yan et al. |
| 2010/0018902 A1 | 1/2010 | Brownscombe et al. |
| 2010/0022789 A1 | 1/2010 | Mignani et al. |
| 2010/0037667 A1 | 2/2010 | Calderon et al. |
| 2010/0043280 A1 | 2/2010 | Morris |
| 2010/0047499 A1 | 2/2010 | Braksmayer et al. |
| 2010/0087671 A1 | 4/2010 | Lemke |
| 2010/0093944 A1 | 4/2010 | Müller et al. |
| 2010/0094034 A1 | 4/2010 | Kaido et al. |
| 2010/0107474 A1 | 5/2010 | Talwar et al. |
| 2010/0113719 A1 | 5/2010 | Patton et al. |
| 2010/0121087 A1 | 5/2010 | Banavali et al. |
| 2010/0130769 A1 | 5/2010 | Banavali et al. |
| 2010/0132252 A1 | 6/2010 | Nakazono |
| 2010/0140136 A1 | 6/2010 | Spilker et al. |
| 2010/0160506 A1 | 6/2010 | Wu et al. |
| 2010/0163459 A1 | 7/2010 | Odueyungbo |
| 2010/0166620 A1 | 7/2010 | Gurski et al. |
| 2010/0167910 A1 | 7/2010 | Odueyungbo |
| 2010/0191008 A1 | 7/2010 | Olson |
| 2010/0212219 A1 | 8/2010 | Siochi et al. |
| 2010/0212220 A1 | 8/2010 | Tirmizi |
| 2010/0223842 A1 | 9/2010 | Thesz et al. |
| 2010/0228042 A1 | 9/2010 | Chun et al. |
| 2010/0234625 A1 | 9/2010 | Papadogianakis et al. |
| 2010/0236984 A1 | 9/2010 | Brookhart et al. |
| 2010/0242348 A1 | 9/2010 | Chen et al. |
| 2010/0243961 A1 | 9/2010 | Hilton et al. |
| 2010/0252485 A1 | 10/2010 | Soane et al. |
| 2010/0263263 A1 | 10/2010 | O'Rear |
| 2010/0264015 A1 | 10/2010 | Portnoff et al. |
| 2010/0282467 A1 | 11/2010 | Hutchison et al. |
| 2010/0305354 A1 | 12/2010 | DuBois |
| 2010/0307051 A1 | 12/2010 | Tremblay et al. |
| 2010/0312012 A1 | 12/2010 | Hannen et al. |
| 2010/0331558 A1 | 12/2010 | Kao et al. |
| 2011/0015419 A1 | 1/2011 | Pendleton et al. |
| 2011/0015434 A1 | 1/2011 | Hannen et al. |
| 2011/0077360 A1 | 3/2011 | Obrecht et al. |
| 2011/0087056 A1 | 4/2011 | Tirtowidjojo et al. |
| 2011/0113679 A1 | 5/2011 | Cohen et al. |

(56) References Cited

U.S. PATENT DOCUMENTS

| | | |
|---|---|---|
| 2011/0160472 A1 | 6/2011 | Lemke et al. |
| 2011/0190524 A1 | 8/2011 | Winde et al. |
| 2011/0198535 A1 | 8/2011 | Meier et al. |
| 2011/0237850 A1 | 9/2011 | Luetkens, Jr. et al. |
| 2011/0252696 A1 | 10/2011 | Franklin et al. |
| 2011/0313180 A1 | 12/2011 | Uptain et al. |
| 2012/0009133 A1 | 1/2012 | Leonard et al. |
| 2012/0035392 A1 | 2/2012 | Kobayashi et al. |
| 2012/0077235 A1 | 3/2012 | Olson |
| 2012/0088943 A1 | 4/2012 | Knuuttila et al. |
| 2012/0116138 A1 | 5/2012 | Goodall et al. |
| 2012/0152723 A1 | 6/2012 | Yoneya |
| 2012/0165293 A1 | 6/2012 | Yiannikouros et al. |
| 2012/0165589 A1 | 6/2012 | Partington |
| 2012/0171090 A1 | 7/2012 | Chang |
| 2012/0178913 A1 | 7/2012 | Lin et al. |
| 2012/0190806 A1 | 7/2012 | Jäkel et al. |
| 2012/0197031 A1 | 8/2012 | Firth et al. |
| 2012/0197032 A1 | 8/2012 | Firth et al. |
| 2012/0271019 A1 | 10/2012 | Drozdzak |
| 2012/0289729 A1 | 11/2012 | Holtcamp et al. |
| 2012/0329941 A1 | 12/2012 | Ong et al. |
| 2013/0085288 A1 | 4/2013 | Snead et al. |

FOREIGN PATENT DOCUMENTS

| | | | | |
|---|---|---|---|---|
| EP | 0116408 A2 * | 8/1984 | ............... | C11B 3/06 |
| EP | 0291033 A1 | 11/1988 | | |
| EP | 0167201 B2 | 11/1995 | | |
| EP | 0168091 B2 | 4/2003 | | |
| EP | 1 728 844 A1 | 12/2006 | | |
| EP | 1810960 A1 | 7/2007 | | |
| FR | 2696450 A1 | 4/1994 | | |
| JP | S56-104847 S | 8/1981 | | |
| JP | S60-174731 A | 9/1985 | | |
| JP | 5-4938 A | 1/1993 | | |
| JP | H10-216524 A | 8/1998 | | |
| JP | 2004-525934 A | 8/2004 | | |
| JP | 2005-523931 A | 8/2005 | | |
| JP | 2007-197443 A | 8/2007 | | |
| JP | 2010-509472 A | 3/2010 | | |
| JP | 2011-515539 A | 5/2011 | | |
| JP | 2012-509985 A | 4/2012 | | |
| WO | WO 94/23836 A1 | 10/1994 | | |
| WO | WO 01/36368 A2 | 5/2001 | | |
| WO | WO 01/83097 A2 | 11/2001 | | |
| WO | WO 02/10114 A2 | 2/2002 | | |
| WO | WO 02/076920 A1 | 10/2002 | | |
| WO | WO 02/083742 A2 | 10/2002 | | |
| WO | WO 2004/037754 A2 | 5/2004 | | |
| WO | WO 2006/043281 A1 | 4/2006 | | |
| WO | WO 2006/052688 A2 | 5/2006 | | |
| WO | WO 2006/076364 A2 | 7/2006 | | |
| WO | WO 2007/027669 A1 | 3/2007 | | |
| WO | WO 2007/027955 A2 | 3/2007 | | |
| WO | WO 2007081987 A2 * | 7/2007 | ............. | C07C 51/36 |
| WO | WO 2007/092632 A2 | 8/2007 | | |
| WO | WO 2007/103460 A2 | 9/2007 | | |
| WO | WO 2007/113530 A2 | 10/2007 | | |
| WO | WO 2008008440 | 1/2008 | | |
| WO | WO 2008/046106 A2 | 4/2008 | | |
| WO | WO 2008/048520 A2 | 4/2008 | | |
| WO | WO 2008/048522 A1 | 4/2008 | | |
| WO | WO 2008/058664 A1 | 5/2008 | | |
| WO | WO 2008/063322 A2 | 5/2008 | | |
| WO | WO 2008/104929 A1 | 9/2008 | | |
| WO | WO 2008140468 A2 * | 11/2008 | ............. | C07C 69/34 |
| WO | WO 2008/152371 A1 | 12/2008 | | |
| WO | WO 2009/007234 A1 | 1/2009 | | |
| WO | WO 2009/020665 A1 | 2/2009 | | |
| WO | WO 2009/020667 A1 | 2/2009 | | |
| WO | WO 2009048459 | 4/2009 | | |
| WO | WO 2009/065229 A1 | 5/2009 | | |
| WO | WO 2009/089591 A1 | 7/2009 | | |
| WO | WO 2010/021740 A1 | 2/2010 | | |
| WO | WO 2010/051268 | 5/2010 | | |
| WO | WO 2010/051268 A1 | 5/2010 | | |
| WO | WO 2010/062958 | 6/2010 | | |
| WO | WO 2010/062958 A1 | 6/2010 | | |
| WO | WO 2010/074738 | 7/2010 | | |
| WO | WO 2010/074738 A1 | 7/2010 | | |
| WO | WO 2010/096549 | 8/2010 | | |
| WO | WO 2010/096549 A2 | 8/2010 | | |
| WO | WO 2010/097519 A2 | 9/2010 | | |
| WO | WO 2010/104844 | 9/2010 | | |
| WO | WO 2010/104844 A2 | 9/2010 | | |
| WO | WO 2010/124030 A1 | 10/2010 | | |
| WO | WO 2010/129051 | 11/2010 | | |
| WO | WO 2011/046872 | 4/2011 | | |
| WO | WO 2011/046872 A2 | 4/2011 | | |
| WO | WO 2011/149789 | 12/2011 | | |
| WO | WO 2012/004489 | 1/2012 | | |
| WO | WO 2012/129479 A2 | 9/2012 | | |

OTHER PUBLICATIONS

Boelhouwer, et al., "Metathesis of Fatty Acid Esters" in JAOCS, 61(2) 425-429, Feb. 1984.*

Seador, et al., "Distillation" in Perry's Chemical Engineer's Handbook, R. H. Perry and D. W. Green, eds., McGraw-Hill, 7th ed., 1997, available on-line Mar. 1, 2001.*

Nordin, et al., "Metathesis of Palm Oil" in Journal of Molecular Catalysis, 65 (1991), 163-172.—month unknown.*

International Search Report and Written Opinion of the International Searching Authority for International Application No. PCT/US2010/052174, dated Apr. 15, 2011, 9 pages.

Ackman, R.G. et al., "Ozonolysis of Unsaturated Fatty Acids," Can. J. Chem., vol. 39, 1961, pp. 1956-1963.

Throckmorton, P.E. et al., "Pilot Run, Plant Design and Cost Analysis for Reductive Ozonolysis of Methyl Soyate," Research and Development Laboratories, 1967, p. 643.

Throckmorton, P.E. et al., "Reductive Ozonolysis of Soybean Oil: Laboratory Optimization of Process Variables," Research and Development Laboratories, p. 641.

Foglia, T.A., et al., "Oxidation of Unsaturated Fatty Acids With Ruthenium and Osmium Tetroxide," J. Am. Oil Chemists' Soc., vol. 54, Nov. 1977, pp. 870A-872A.

Rüsch gen. Klaas, M., et al., "Transition-Metal Catalyzed Oxidative Cleavage of Unsaturated Fatty Acids," Fat Sci. Technol., vol. 95(10), 1995, pp. 359-367.

Turnwald, S.E., et al., "Oleic Acid Oxidation Using Hydrogen Peroxide in Conjunction With Transition Metal Catalysis," Journal of Materials Science Letters, vol. 17, 1998, pp. 1305-1307.

Oakley, Michael A., et al., "Practical Dihydroxylation and C-C Cleavage of Unsaturated Fatty Acids," Journal of Molecular Catalysis A: Chemical, vol. 150, 1999, pp. 105-111.

Noureddini, H. et al., "Liquid-Phase Catalytic Oxidation of Unsaturated Fatty Acids," Journal of American Oil Chemists' Society, vol. 76, No. 3, 1999, pp. 305-312.

Santacesaria, E., et al., "Oxidative Cleavage of the Double Bond of Monoenic Fatty Chains in Two Steps: A New Promising Route to Azelaic Acid and Other Industrial Products," Ind. Eng. Chem. Res., vol. 39, 2000, pp. 2766-2771.

Santacesaria, E. et al., "Double Bond Oxidative Cleavage of Monoenic Fatty Chains," Catalysis Today, vol. 79-80, 2003, pp. 59-65.

Bryan, Tom, "Adsorbing It All," Biodiesel Magazine, Mar. 2005, pp. 40-43.

Patel, Jim et al., "High Conversion and Productive Catalyst Turnovers in Cross-Metathesis Reactions of Natural Oils With 2-Butene," Green Chem., vol. 8, 2006, pp. 450-454.

Kram, Jerry W., "Cleaner and Clearer," Biodiesel Magazine, Jan. 2008, 4 pages.

Erhan et al., "Drying Properties of Metathesized Soybean Oil," Journal of American Oil Chemists' Society, AOCS Press, vol. 74, No. 6, 1997, pp. 703-706.

Ahn, Y.M. et al., "A Convenient Method for the Efficient Removal of Ruthenium Byproducts Generated during Olefin Metathesis Reactions," Org. Lett., 2001, vol. 3, pp. 1411-1413.

(56) References Cited

OTHER PUBLICATIONS

Bourgeois, Damien et al., "The Cl$_2$(PCy3)(IMes)Ru(=CHPh) catalyst: olefin metathesis versus olefin isomerization," Journal of Organic Metallic Chemistry, vol. 643-644, 2002, pp. 247-252.

Cho, J.H. et al., "An Efficient Method for Removal of Ruthenium Byproucts from Olefin Metathesis Reactions," Org. Lett., 2003, vol. 5, pp. 531-533.

Cotton, F.A. et al., Advanced Inorganic Chemistry, Fifth Edition, New York, John Wiley & Sons, 1988, pp. 382-443.

Formentin, P. et al., "Reactivity of Grubbs' Catalysts with Urea- and Amide-Substituted Olefins. Metathesis and Isomerization," J. Org. Chem., 2005, vol. 70, pp. 8235-8238.

Galan, B. R. et al., "A Rapid and Simple Cleanup Procedure for Metathesis Reactions," Org. Lett., 2007, vol. 9, pp. 1203-1206.

Gimeno, N. et al., "Phenylphosphoric Acid as a New Additive to Inhibit Olefin Isomerization in Ruthenium-Catalyzed Metathesis Reactions," Eur. J. Org. Chem., 2007, pp. 918-924.

Hong, S.H. et al., "Prevention of Undesirable Isomerization During Olefin Metathesis," J. Am. Chem. Soc., 2005, vol. 127, pp. 17160-17161.

James, B.R. et al., "Developments in the Chemistry of Tris(hydroxymehtyl)phosphine," Coordination Chemistry Reviews, 2010, vol. 254, pp. 420-430.

Knight, D.W. et al., "A Simple Oxidative Procedure for the Removal of Ruthenium Residues from Metathesis Reaction Products," Tetrahedron Letters, 2010, vol. 51, pp. 638-640.

Maynard et al., "Purification Technique for the Removal of Ruthenium from Olefin Metathesis Reaction Products," Tetrahedron Letters, vol. 40, No. 22, 1999, pp. 4137-4140.

McEleney, K. et al., "Functionalized Mesoporous Silicates for the Removal of Ruthenium from Reaction Mixtures," Org. Lett., 2006, vol. 8, pp. 2663-2666.

Mol, "Metathesis of unsaturated fatty acid esters and fatty oils," Journal of Molecualr Catalysis, vol. 90, 1994, pp. 185-199.

Mol, "Catalytic Metathesis of Unsaturated Fatty Acid Esters and Oils," Topics in Catalysis, vol. 27, No. 1-4, 2004, pp. 97-104.

Othmer, Kirk, "Metathesis," Encyclopedia of Chemical Technology, vol. 26, Dec. 2005, pp. 920-958.

Paquette, L.A. et al., "A Convenient Method for Removing All Highly-Colored Byproducts Generated During Olefin Metathesis Reactions," Org. Lett., 2000, vol. 2, pp. 1259-1261.

Patel, Jim et al., "Cross-metathesis of unsaturated natural oils with 2-butene, High conversion and productive catalyst turnovers," Chem. Commun., 2005, pp. 5546-5547.

Pederson, R.L. et al., "Applications of Olefin Cross Metathesis to Commercial Products," Advanced Synthesis & Catalysts, 2002, vol. 344, pp. 728-735.

Wang, H. et al., "Development of a Robust Ring-Closing Metathesis Reaction in the Synthesis of SB-462795, a Cathepsin K Inhibitor," Organic Process Research & Development, 2008, vol. 12, pp. 226-234.

International Preliminary Report on Patentability issued in PCT Patent Application No. PCT/US2012/070255, mailed Jul. 3, 2014, 8 pages.

International Preliminary Report on Patentability issued in PCT Patent Application No. PCT/US2012/070275, mailed Jul. 3, 2014, 8 pages.

International Search Report and Written Opinion of the International Searching Authority issued in PCT Patent Application No. PCT/US2014/023530, mailed May 27, 2014, 11 pages.

International Search Report and Written Opinion of the International Searching Authority issued in corresponding PCT Patent Application No. PCT/US2013/063861, mailed Mar. 24, 2014, 12 pages.

Rybak et al., "Cross-metathesis of fatty acid derivatives with methyl acrylate: renewable raw materials for the chemical industry" Green Chem, 9, 2007, pp. 1356-1361.

Forman et al., "Improved cross-metathesis of acrylate esters catalyzed by 2$^{nd}$ generation ruthenium carbine complexes" Journal of Organometallic Chemistry, 690, 2005, pp. 5863-5866.

Schrock, "High Oxidation State Multiple Metal-Carbon Bonds" Chem. Rev., 102, 2002, pp. 145-179.

Schrock et al., "Molybdenum and Tungsten Imido Alkylidene Complexes as Efficient Olefin-Metathesis Catalysts" Angew, Chem. Int. Ed. , 42, 2003, pp. 4592-4633.

Schrock, "Recent Advances in High Oxidation State Mo and W Imido Alkylidene Chemistry" Chem. Rev., 109, 2009, pp. 3211-3226.

Warwel et al., "Metathesis of unsaturated fatty acid esters. A simple approach to long-chained dicarboxylic acids" Lipid Fat Science Technology, vol. 94, No. 9, Jan. 1992, pp. 323-328.

Warwel et al., "Polymers and surfactants on the basis of renewable resources" Chemosphere, Pergamon Press, Oxford, GB, vol. 1, Jan. 2001, pp. 39-48.

Verkuijlen et al., "Metathesis of Unsaturated Fatty Esters" Fette, Seifen Anstrichmittel Hamburg, DE, vol. 78, No. 11, Jan. 1976, pp. 444-447.

International Search Report and Written Opinion of the International Searching Authority issued in PCT Patent Application No. PCT/US2014/023306, mailed Jul. 17, 2014, 11 pages.

Office Action issued in Japanese Application No. 2012-534266, mailed Aug. 29, 2014, 11 pages.

* cited by examiner

METHODS OF REFINING NATURAL OIL FEEDSTOCKS

CROSS REFERENCE TO RELATED APPLICATIONS

This application claims the benefit of U.S. Provisional Patent Application No. 61/250,743, filed Oct. 12, 2009, which is incorporated herein by reference.

BACKGROUND

Metathesis is a catalytic reaction generally known in the art that involves the interchange of alkylidene units among compounds containing one or more double bonds (e.g., olefinic compounds) via the formation and cleavage of the carbon-carbon double bonds. Metathesis may occur between two like molecules (often referred to as self-metathesis) and/or it may occur between two different molecules (often referred to as cross-metathesis). Self-metathesis may be represented schematically as shown in Equation I.

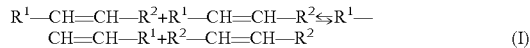
(I)

wherein $R^1$ and $R^2$ are organic groups.

Cross-metathesis may be represented schematically as shown in Equation II.

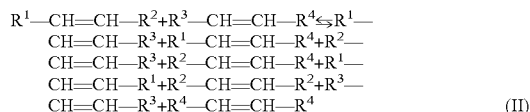
(II)

wherein $R^1$, $R^2$, $R^3$, and $R^4$ are organic groups.

In recent years, there has been an increased demand for environmentally friendly techniques for manufacturing materials typically derived from petroleum sources. For example, researchers have been studying the feasibility of manufacturing biofuels, waxes, plastics, and the like, using natural oil feedstocks, such as vegetable and seed-based oils. In one non-limiting example, metathesis catalysts are used to manufacture candle wax, as described in PCT/US2006/000822, which is herein incorporated by reference in its entirety. Metathesis reactions involving natural oil feedstocks offer promising solutions for today and for the future.

Natural oil feedstocks of interest include non-limiting examples such as natural oils (e.g., vegetable oils, fish oil, animal fats) and derivatives of natural oils, such as fatty acids and fatty acid alkyl (e.g., methyl) esters. These feedstocks may be converted into industrially useful chemicals (e.g., waxes, plastics, cosmetics, biofuels, etc.) by any number of different metathesis reactions. Significant reaction classes include, as non-limiting examples, self-metathesis, cross-metathesis with olefins, and ring-opening metathesis reactions. Representative non-limiting examples of useful metathesis catalysts are provided below. Metathesis catalysts can be expensive and, therefore, it is desirable to improve the efficiency of the metathesis catalyst.

In recent years, there has been an increased demand for petroleum-based transportation fuels. Concerns exist that the world's petroleum production may not be able to keep up with demand. Additionally, the increased demand for petroleum-based fuels has resulted in a higher production of greenhouse gases. In particular, the airline industry accounts for greater than 10% of the greenhouse gases within the United States. Due to the increased demand for fuel and increased production of greenhouse gases, there is a need to explore methods of producing environmentally-friendly, alternative fuel sources. In particular, there is a need to explore methods of producing environmentally friendly fuel compositions and specialty chemicals from a natural feedstock.

SUMMARY

Methods are disclosed for refining a natural oil feedstock through a metathesis reaction of the natural oil feedstock in the presence of a metathesis catalyst.

In one embodiment, the method comprises reacting a feedstock comprising a natural oil in the presence of a metathesis catalyst under conditions sufficient to form a metathesized product, wherein the metathesized product comprises olefins and esters. The method further comprises separating the olefins from the esters. The method further comprises transesterifying the esters in the presence of an alcohol to form a transesterified product.

In certain embodiments, the method further comprises treating the feedstock prior to reacting the feedstock, under conditions sufficient to diminish catalyst poisons in the feedstock. In some embodiments, the feedstock is chemically treated through a chemical reaction to diminish the catalyst poisons. In other embodiments, the feedstock is heated to a temperature greater than 100° C. in the absence of oxygen and held at the temperature for a time sufficient to diminish the catalyst poisons.

In certain embodiments, the method further comprises separating the metathesis catalyst from the olefins and esters with a water soluble phosphine reagent.

In certain embodiments, the metathesis catalyst is dissolved in a solvent prior to the metathesis reaction. In some embodiments, the solvent is toluene.

In certain embodiments, the method further comprises hydrogenating the olefins to form a fuel composition. In some embodiments, the fuel composition comprises a jet fuel composition having a carbon number distribution between 5 and 16. In other embodiments, the fuel composition comprises a diesel fuel composition having a carbon number distribution between 8 and 25. In some embodiments, the fuel composition is: (a) a kerosene-type jet fuel having a carbon number distribution between 8 and 16, a flash point between approximately 38° C. and approximately 66° C., an auto ignition temperature of approximately 210° C., and a freeze point between approximately −47° C. and approximately −40° C.; (b) a naphtha-type jet fuel having a carbon number distribution between 5 and 15, a flash point between approximately −23° C. and approximately 0° C., an auto ignition temperature of approximately 250° C.; and a freeze point of approximately −65° C.; or (c) a diesel fuel having a carbon number distribution between 8 and 25, a specific gravity of between approximately 0.82 and approximately 1.08 at about 15.6° C., a cetane number of greater than approximately 40; and a distillation range between approximately 180° C. and approximately 340° C.

In certain embodiments, the method further comprises oligomerizing the olefins to form at least one of: poly-alpha-olefins, poly-internal-olefins, mineral oil replacements, or biodiesel.

In certain embodiments, the method further comprises separating glycerin from the transesterified product through a liquid-liquid separation, washing the transesterified product with water to further remove glycerin, and drying the transesterified product to separate the water from the transesterified product. In some embodiments, the method further comprises distilling the transesterified product to separate at least one specialty chemical selected from the group consisting of: 9-decenoic acid ester, 9-undecenoic acid ester, 9-dodecenoic acid ester, individually or in combinations thereof. In some additional embodiments, the method further comprises hydrolyzing the at least one specialty chemical, thereby forming at least one acid selected from the group consisting of: 9-decenoic acid, 9-undecenoic acid, 9-dodecenonic acid, individually or in combinations thereof. In certain embodiments, the hydrolyzing step further yields alkali metal salts and alkaline earth metal salts, individually or in combinations thereof, of the at least one acid.

In certain embodiments, the method comprises reacting the transesterified product with itself to form a dimer.

In certain embodiments, the reacting step comprises a self-metathesis reaction between the feedstock and itself. In other embodiments, the reacting step comprises a cross-metathesis reaction between a low-molecular-weight olefin and the feedstock. In some embodiments, the low-molecular-weight olefin comprises at least one low-molecular-weight olefin selected from the group consisting of ethylene, propylene, 1-butene, 2-butene, individually or in combinations thereof. In some embodiments, the low-molecular-weight olefin is an alpha-olefin. In one embodiment, the low-molecular-weight olefin comprises at least one branched olefin having a carbon number between 4 and 10.

In another embodiment, the method comprises reacting a feedstock comprising a natural oil in the presence of a metathesis catalyst under conditions sufficient to form a metathesized product, wherein the metathesized product comprises olefins and esters. The method further comprises separating the olefins from the esters. The method further comprises hydrogenating the olefins under conditions sufficient to form a fuel composition.

In certain embodiments, the fuel composition comprises a jet fuel composition having a carbon number distribution between 5 and 16. In other embodiments, the fuel composition comprises a diesel fuel composition having a carbon number distribution between 8 and 25. In some embodiments, the fuel composition is: (a) a kerosene-type jet fuel having a carbon number distribution between 8 and 16, a flash point between approximately 38° C. and approximately 66° C., an auto ignition temperature of approximately 210° C., and a freeze point between approximately −47° C. and approximately −40° C.; (b) a naphtha-type jet fuel having a carbon number distribution between 5 and 15, a flash point between approximately −23° C. and approximately 0° C., an auto ignition temperature of approximately 250° C.; and a freeze point of approximately −65° C.; or (c) a diesel fuel having a carbon number distribution between 8 and 25, a specific gravity of between approximately 0.82 and approximately 1.08 at about 15.6° C., a cetane number of greater than approximately 40; and a distillation range between approximately 180° C. and approximately 340° C.

In certain embodiments, the method further comprises flash-separating a light end stream from the metathesized product prior to separating the olefins from the esters, the light end stream having a majority of hydrocarbons with carbon number between 2 and 4.

In certain embodiments, the method further comprises separating a light end stream from the olefins prior to hydrogenating the olefins, the light end stream having a majority of hydrocarbons with carbon numbers between 3 and 8.

In certain embodiments, the method further comprises separating a $C_{18+}$ heavy end stream from the olefins prior to hydrogenating the olefins, the heavy end stream having a majority of hydrocarbons with carbon numbers of at least 18.

In certain embodiments, the method further comprises separating a $C_{18+}$ heavy end stream from the fuel composition, the heavy end stream having a majority of hydrocarbons with carbon numbers of at least 18.

In certain embodiments, the method further comprises isomerizing the fuel composition, wherein a fraction of normal-paraffin compounds in the fuel composition are isomerized into iso-paraffin compounds.

In certain embodiments, the reacting step comprises a self-metathesis reaction between the feedstock and itself. In other embodiments, the reacting step comprises a cross-metathesis reaction between a low-molecular-weight olefin and the feedstock.

In another embodiment, the method comprises reacting a feedstock comprising a natural oil in the presence of a metathesis catalyst under conditions sufficient to form a metathesized product, wherein the metathesized product comprises olefins and esters. The method further comprises hydrogenating the metathesized product thereby producing a fuel composition and at least partially saturated esters. The method further comprises separating the fuel composition from the at least partially saturated esters. The method may further comprise isomerizing the fuel composition, wherein a portion of normal paraffins are isomerized into iso-paraffins, therein forming an isomerized fuel composition. The method may further comprise separating a center-cut fuel stream from the fuel composition or isomerized fuel composition.

DETAILED DESCRIPTION

Figure 1:
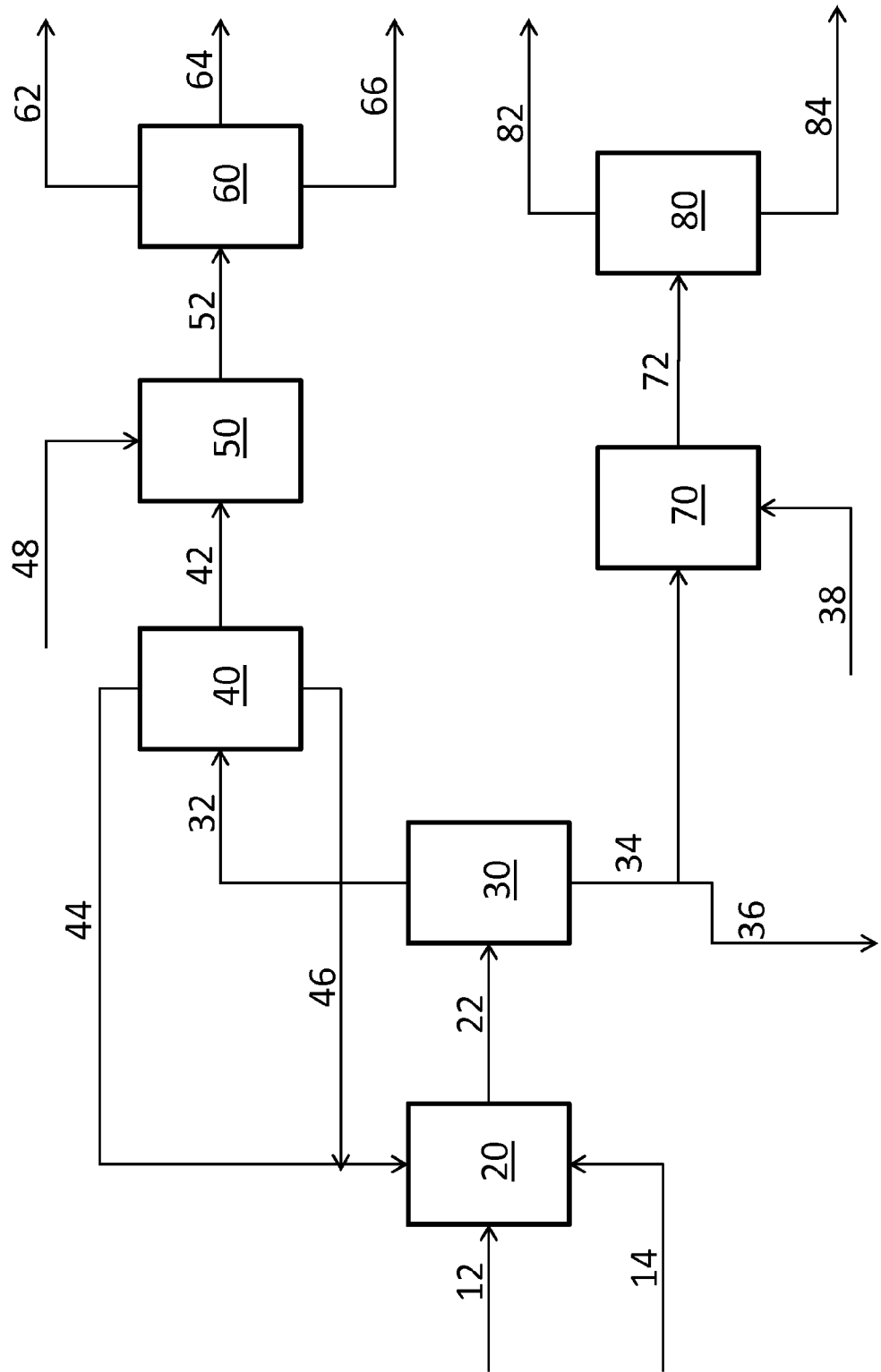
FIG. 1 is a schematic diagram of one embodiment of a process to produce a fuel composition and a transesterified product from a natural oil.

The present application relates to methods of refining a natural oil feedstock through the metathesis reaction of the natural oil feedstock.

As used herein, the singular forms "a," "an," and "the" include plural referents unless the context clearly dictates otherwise. For example, reference to "a substituent" encompasses a single substituent as well as two or more substituents, and the like.

As used herein, the terms "for example," "for instance," "such as," or "including" are meant to introduce examples that further clarify more general subject matter. Unless otherwise specified, these examples are provided only as an aid for understanding the applications illustrated in the present disclosure, and are not meant to be limiting in any fashion.

As used herein, the following terms have the following meanings unless expressly stated to the contrary. It is understood that any term in the singular may include its plural counterpart and vice versa.

As used herein, the term "metathesis catalyst" includes any catalyst or catalyst system that catalyzes a metathesis reaction.

As used herein, the terms "natural oils," "natural feedstocks," or "natural oil feedstocks" may refer to oils derived from plants or animal sources. The term "natural oil" includes natural oil derivatives, unless otherwise indicated. Examples of natural oils include, but are not limited to, vegetable oils, algae oils, animal fats, tall oils, derivatives of these oils, combinations of any of these oils, and the like. Representative non-limiting examples of vegetable oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, pennycress oil, camelina oil, and castor oil. Representative non-limiting examples of animal fats include lard, tallow, poultry fat, yellow grease, and fish oil. Tall oils are by-products of wood pulp manufacture.

As used herein, the term "natural oil derivatives" may refer to the compounds or mixture of compounds derived from the natural oil using any one or combination of methods known in the art. Such methods include saponification, transesterification, esterification, hydrogenation (partial or full), isomerization, oxidation, and reduction. Representative non-limiting examples of natural oil derivatives include gums, phospholipids, soapstock, acidulated soapstock, distillate or distillate sludge, fatty acids and fatty acid alkyl ester (e.g. non-limiting examples such as 2-ethylhexyl ester), hydroxy substituted variations thereof of the natural oil. For example, the natural oil derivative may be a fatty acid methyl ester ("FAME") derived from the glyceride of the natural oil. In some embodiments, a feedstock includes canola or soybean oil, as a non-limiting example, refined, bleached, and deodorized soybean oil (i.e., RBD soybean oil). Soybean oil typically comprises about 95% weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9,12-octadecadienoic acid), and linolenic acid (9,12,15-octadecatrienoic acid).

As used herein, the term "low-molecular-weight olefin" may refer to any one or combination of unsaturated straight, branched, or cyclic hydrocarbons in the $C_2$ to $C_{14}$ range. Low-molecular-weight olefins include "alpha-olefins" or "terminal olefins," wherein the unsaturated carbon-carbon bond is present at one end of the compound. Low-molecular-weight olefins may also include dienes or trienes. Examples of low-molecular-weight olefins in the $C_2$ to $C_6$ range include, but are not limited to: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. Other possible low-molecular-weight olefins include styrene and vinyl cyclohexane. In certain embodiments, it is preferable to use a mixture of olefins, the mixture comprising linear and branched low-molecular-weight olefins in the $C_4$-$C_{10}$ range. In one embodiment, it may be preferable to use a mixture of linear and branched $C_4$ olefins (i.e., combinations of: 1-butene, 2-butene, and/or isobutene). In other embodiments, a higher range of $C_{11}$-$C_{14}$ may be used.

As used herein, the terms "metathesize" and "metathesizing" may refer to the reacting of a feedstock in the presence of a metathesis catalyst to form a "metathesized product" comprising a new olefinic compound. Metathesizing may refer to cross-metathesis (a.k.a. co-metathesis), self-metathesis, ring-opening metathesis, ring-opening metathesis polymerizations ("ROMP"), ring-closing metathesis ("RCM"), and acyclic diene metathesis ("ADMET"). As a non-limiting example, metathesizing may refer to reacting two triglycerides present in a natural feedstock (self-metathesis) in the presence of a metathesis catalyst, wherein each triglyceride has an unsaturated carbon-carbon double bond, thereby forming a new mixture of olefins and esters which may include a triglyceride dimer. Such triglyceride dimers may have more than one olefinic bond, thus higher olegomers also may form. Additionally, metathesizing may refer to reacting an olefin, such as ethylene, and a triglyceride in a natural feedstock having at least one unsaturated carbon-carbon double bond, thereby forming new olefinic molecules as well as new ester molecules (cross-metathesis).

As used herein, the terms "ester" and "esters" may refer to compounds having the general formula: R—COO—R', wherein R and R' denote any alkyl or aryl group, including those bearing a substituent group. In certain embodiments, the term "ester" or "esters" may refer to a group of compounds with the general formula described above, wherein the compounds have different carbon lengths.

As used herein, the terms "olefin" and "olefins" may refer to hydrocarbon compounds having at least one unsaturated carbon-carbon double bond. In certain embodiments, the term "olefin" or "olefins" may refer to a group of unsaturated carbon-carbon double bond compounds with different carbon lengths. It is noted that an olefin may also be an ester, and an ester may also be an olefin, if the R or R' group contains an unsaturated carbon-carbon double bond. Unless specified otherwise, an olefin refers to compounds not containing the ester functionality, while an ester may include compounds containing the olefin functionality.

As used herein, the terms "paraffin" and "paraffins" may refer to hydrocarbon compounds having only single carbon-carbon bonds, having the general formula $C_nH_{2n+2}$, where, in certain embodiments, n is greater than about 20.

As used herein, the terms "isomerization," "isomerizes," or "isomerizing" may refer to the reaction and conversion of straight-chain hydrocarbon compounds, such as normal paraffins, into branched hydrocarbon compounds, such as iso-paraffins. The isomerization of an olefin or an unsaturated ester indicates the shift of the carbon-carbon double bond to another location in the molecule or it indicates a change in the geometry of the compound at the carbon-carbon double bond (e.g. cis to trans). As a non-limiting example, n-pentane may be isomerized into a mixture of n-pentane, 2-methylbutane, and 2,2-dimethylpropane. Isomerization of normal paraffins may be used to improve the overall properties of a fuel composition. Additionally, isomerization may refer to the conversion of branched paraffins into further, more branched paraffins.

As used herein, the term "yield" may refer to the total weight of fuel produced from the metathesis and hydrogenation reactions. It may also refer to the total weight of the fuel following a separation step and/or isomerization reaction. It may be defined in terms of a yield %, wherein the total weight of the fuel produced is divided by the total weight of the natural oil feedstock and, in some embodiments, low-molecular-weight olefin, combined.

As used herein, the terms "fuels" and "fuel compositions" refer to materials meeting required specifications or to blend components that are useful in formulating fuel compositions but, by themselves, do not meet all of the required specifications for a fuel.

As used herein, the term "jet fuel" or "aviation fuel" may refer to kerosene or naphtha-type fuel cuts, or military-grade jet fuel compositions. "Kerosene-type" jet fuel (including Jet A and Jet A-1) has a carbon number distribution between about 8 and about 16. Jet A and Jet A-1 typically have a flash point of at least approximately 38° C., an auto ignition temperature of approximately 210° C., a freeze point less than or equal to approximately −40° C. for Jet A and −47° C. for Jet A-1, a density of approximately 0.8 g/cc at 15° C., and an energy density of approximately 42.8-43.2 MJ/kg. "Naphtha-type" or "wide-cut" jet fuel (including Jet B) has a carbon number distribution between about 5 and about 15. Jet B typically comprises a flash point below approximately 0° C., an auto ignition temperature of approximately 250° C., a freeze point of approximately −51° C., a density of approximately 0.78 g/cc, and an energy density of approximately 42.8-43.5 MJ/kg. "Military grade" jet fuel refers to the Jet Propulsion or "JP" numbering system (JP-1, JP-2, JP-3, JP-4, JP-5, JP-6, JP-7, JP-8, etc.). Military grade jet fuels may comprise alternative or additional additives to have higher flash points than Jet A, Jet A-1, or Jet B in order to cope with heat and stress endured during supersonic flight.

As used herein, the term "diesel fuel" may refer to a hydrocarbon composition having the following property characteristics, including a carbon number distribution between about 8 and about 25. Diesel fuels also typically have a specific gravity of approximately 0.82-1.08 at 15.6° C. (60° F.), based on water having a specific gravity of 1 at 60° F. Diesel fuels typically comprise a distillation range between approximately 180-340° C. (356-644° F.). Additionally, diesel fuels have a minimum cetane index number of approximately 40.

As used herein, the term "carbon number distribution" may refer to the range of compounds present in a composition, wherein each compound is defined by the number of carbon atoms present. As a non-limiting example, a naphtha-type jet fuel typically comprises a distribution of hydrocarbon compounds wherein a majority of those compounds have between 5 and 15 carbon atoms each. A kerosene-type jet fuel typically comprises a distribution of hydrocarbon compounds wherein a majority of those compounds have between 8 and 16 carbon atoms each. A diesel fuel typically comprises a distribution of hydrocarbon compounds wherein a majority of those compounds have between 8 and 25 carbon atoms each.

As used herein, the term "energy density" may refer to the amount of energy stored in a given system per unit mass (MJ/kg) or per unit volume (MJ/L), where MJ refer to million Joules. As a non-limiting example, the energy density of kerosene- or naphtha-type jet fuel is typically greater than about 40 MJ/kg.

A number of valuable compositions may be targeted through the self-metathesis reaction of a natural oil feedstock, or the cross-metathesis reaction of the natural oil feedstock with a low-molecular-weight olefin, in the presence of a metathesis catalyst. Such valuable compositions may include fuel compositions, non-limiting examples of which include jet, kerosene, or diesel fuel. Additionally, transesterified products may also be targeted, non-limiting examples of which include: fatty acid methyl esters; biodiesel; 9-decenoic acid ("9DA") esters, 9-undecenoic acid ("9UDA") esters, and/or 9-dodecenoic acid ("9DDA") esters; 9DA, 9UDA, and/or 9DDA; alkali metal salts and alkaline earth metal salts of 9DA, 9UDA, and/or 9DDA; dimers of the transesterified products; and mixtures thereof.

In certain embodiments, prior to a metathesis reaction, a natural oil feedstock may be treated to render the natural oil more suitable for the subsequent metathesis reaction. In certain embodiments, the natural oil preferably is a vegetable oil or vegetable oil derivative, such as soybean oil.

In one embodiment, the treatment of the natural oil involves the removal of catalyst poisons, such as peroxides, which may potentially diminish the activity of the metathesis catalyst. Non-limiting examples of natural oil feedstock treatment methods to diminish catalyst poisons include those described in PCT/US2008/09604, PCT/US2008/09635, and U.S. patent application Ser. Nos. 12/672,651 and 12/672,652, herein incorporated by reference in their entireties. In certain embodiments, the natural oil feedstock is thermally treated by heating the feedstock to a temperature greater than 100° C. in the absence of oxygen and held at the temperature for a time sufficient to diminish catalyst poisons in the feedstock. In other embodiments, the temperature is between approximately 100° C. and 300° C., between approximately 120° C. and 250° C., between approximately 150° C. and 210° C., or approximately between 190 and 200° C. In one embodiment, the absence of oxygen is achieved by sparging the natural oil feedstock with nitrogen, wherein the nitrogen gas is pumped into the feedstock treatment vessel at a pressure of approximately 10 atm (150 psig).

In certain embodiments, the natural oil feedstock is chemically treated under conditions sufficient to diminish the catalyst poisons in the feedstock through a chemical reaction of the catalyst poisons. In certain embodiments, the feedstock is treated with a reducing agent or a cation-inorganic base composition. Non-limiting examples of reducing agents include bisulfate, borohydride, phosphine, thiosulfate, individually or combinations thereof.

In certain embodiments, the natural oil feedstock is treated with an adsorbent to remove catalyst poisons. In one embodiment, the feedstock is treated with a combination of thermal and adsorbent methods. In another embodiment, the feedstock is treated with a combination of chemical and adsorbent methods. In another embodiment, the treatment involves a partial hydrogenation treatment to modify the natural oil feedstock's reactivity with the metathesis catalyst. Additional non-limiting examples of feedstock treatment are also described below when discussing the various metathesis catalysts.

Additionally, in certain embodiments, the low-molecular-weight olefin may also be treated prior to the metathesis reaction. Like the natural oil treatment, the low-molecular-weight olefin may be treated to remove poisons that may impact or diminish catalyst activity.

As shown in FIG. 1, after this optional treatment of the natural oil feedstock and/or low-molecular-weight olefin, the natural oil 12 is reacted with itself, or combined with a low-molecular-weight olefin 14 in a metathesis reactor 20 in the presence of a metathesis catalyst. Metathesis catalysts and metathesis reaction conditions are discussed in greater detail below. In certain embodiments, in the presence of a metathesis catalyst, the natural oil 12 undergoes a self-metathesis reaction with itself. In other embodiments, in the presence of the metathesis catalyst, the natural oil 12 undergoes a cross-metathesis reaction with the low-molecular-weight olefin 14. In certain embodiments, the natural oil 12 undergoes both self- and cross-metathesis reactions in parallel metathesis reactors. The self-metathesis and/or cross-metathesis reaction form a metathesized product 22 wherein the metathesized product 22 comprises olefins 32 and esters 34.

In certain embodiments, the low-molecular-weight olefin 14 is in the $C_2$ to $C_6$ range. As a non-limiting example, in one embodiment, the low-molecular-weight olefin 14 may comprise at least one of the following: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. In another embodiment, the low-molecular-weight olefin 14 comprises at least one of styrene and vinyl cyclohexane. In another embodiment, the low-molecular-weight olefin 14 may comprise at least one of ethylene, propylene, 1-butene, 2-butene, and isobutene. In another embodiment, the low-molecular-weight olefin 14 comprises at least one alpha-olefin or terminal olefin in the $C_2$ to $C_{10}$ range.

In another embodiment, the low-molecular-weight olefin 14 comprises at least one branched low-molecular-weight olefin in the $C_4$ to $C_{10}$ range. Non-limiting examples of branched low-molecular-weight olefins include isobutene, 3-methyl-1-butene, 2-methyl-3-pentene, and 2,2-dimethyl-3-pentene. By using these branched low-molecular-weight olefins in the metathesis reaction, the methathesized product will include branched olefins, which can be subsequently hydrogenated to iso-paraffins. In certain embodiments, the branched low-molecular-weight olefins may help achieve the desired performance properties for a fuel composition, such as jet, kerosene, or diesel fuel.

As noted, it is possible to use a mixture of various linear or branched low-molecular-weight olefins in the reaction to achieve the desired metathesis product distribution. In one embodiment, a mixture of butenes (1-butene, 2-butenes, and, optionally, isobutene) may be employed as the low-molecular-weight olefin, offering a low cost, commercially available feedstock instead a purified source of one particular butene. Such low cost mixed butene feedstocks are typically diluted with n-butane and/or isobutane.

In certain embodiments, recycled streams from downstream separation units may be introduced to the metathesis reactor 20 in addition to the natural oil 12 and, in some embodiments, the low-molecular-weight olefin 14. For instance, in some embodiments, a $C_2$-$C_6$ recycle olefin stream or a $C_3$-$C_4$ bottoms stream from an overhead separation unit may be returned to the metathesis reactor. In one embodiment, as shown in FIG. 1, a light weight olefin stream 44 from an olefin separation unit 40 may be returned to the metathesis reactor 20. In another embodiment, the $C_3$-$C_4$ bottoms stream and the light weight olefin stream 44 are combined together and returned to the metathesis reactor 20. In another embodiment, a $C_{15+}$ bottoms stream 46 from the olefin separation unit 40 is returned to the metathesis reactor 20. In another embodiment, all of the aforementioned recycle streams are returned to the metathesis reactor 20.

The metathesis reaction in the metathesis reactor 20 produces a metathesized product 22. In one embodiment, the metathesized product 22 enters a flash vessel operated under temperature and pressure conditions which target $C_2$ or $C_2$-$C_3$ compounds to flash off and be removed overhead. The $C_2$ or $C_2$-$C_3$ light ends are comprised of a majority of hydrocarbon compounds having a carbon number of 2 or 3. In certain embodiments, the $C_2$ or $C_2$-$C_3$ light ends are then sent to an overhead separation unit, wherein the $C_2$ or $C_2$-$C_3$ compounds are further separated overhead from the heavier compounds that flashed off with the $C_2$-$C_3$ compounds. These heavier compounds are typically $C_3$-$C_5$ compounds carried overhead with the $C_2$ or $C_2$-$C_3$ compounds. After separation in the overhead separation unit, the overhead $C_2$ or $C_2$-$C_3$ stream may then be used as a fuel source. These hydrocarbons have their own value outside the scope of a fuel composition, and may be used or separated at this stage for other valued compositions and applications. In certain embodiments, the bottoms stream from the overhead separation unit containing mostly $C_3$-$C_5$ compounds is returned as a recycle stream to the metathesis reactor. In the flash vessel, the metathesized product 22 that does not flash overhead is sent downstream for separation in a separation unit 30, such as a distillation column.

Prior to the separation unit 30, in certain embodiments, the metathesized product 22 may be introduced to an adsorbent bed to facilitate the separation of the metathesized product 22 from the metathesis catalyst. In one embodiment, the adsorbent is a clay bed. The clay bed will adsorb the metathesis catalyst, and after a filtration step, the metathesized product 22 can be sent to the separation unit 30 for further processing. In another embodiment, the adsorbent is a water soluble phosphine reagent such as tris hydroxymethyl phosphine (THMP). Catalyst may be separated with a water soluble phosphine through known liquid-liquid extraction mechanisms by decanting the aqueous phase from the organic phase. In other embodiments, the metathesized product 22 may be contacted with a reactant to deactivate or to extract the catalyst.

In the separation unit 30, in certain embodiments, the metathesized product 22 is separated into at least two product streams. In one embodiment, the metathesized product 22 is sent to the separation unit 30, or distillation column, to separate the olefins 32 from the esters 34. In another embodiment, a byproduct stream comprising $C_7$'s and cyclohexadiene may be removed in a side-stream from the separation unit 30. In certain embodiments, the separated olefins 32 may comprise hydrocarbons with carbon numbers up to 24. In certain embodiments, the esters 34 may comprise metathesized glycerides. In other words, the lighter end olefins 32 are preferably separated or distilled overhead for processing into olefin compositions, while the esters 34, comprised mostly of compounds having carboxylic acid/ester functionality, are drawn into a bottoms stream. Based on the quality of the separation, it is possible for some ester compounds to be carried into the overhead olefin stream 32, and it is also possible for some heavier olefin hydrocarbons to be carried into the ester stream 34.

In one embodiment, the olefins 32 may be collected and sold for any number of known uses. In other embodiments, the olefins 32 are further processed in an olefin separation unit 40 and/or hydrogenation unit 50 (where the olefinic bonds are saturated with hydrogen gas 48, as described below). In other embodiments, esters 34 comprising heavier end glycerides and free fatty acids are separated or distilled as a bottoms product for further processing into various products. In certain embodiments, further processing may target the production of the following non-limiting examples: fatty acid methyl esters; biodiesel; 9DA esters, 9UDA esters, and/or 9DDA esters; 9DA, 9UDA, and/or 9DDA; alkali metal salts and alkaline earth metal salts of 9DA, 9UDA, and/or 9DDA; diacids, and/or diesters of the transesterified products; and mixtures thereof. In certain embodiments, further processing may target the production of $C_{15}$-$C_{18}$ fatty acids and/or esters. In other embodiments, further processing may target the production of diacids and/or diesters. In yet other embodiments, further processing may target the production of compounds having molecular weights greater than the molecular weights of stearic acid and/or linolenic acid.

As shown in FIG. 1, regarding the overhead olefins 32 from the separation unit 30, the olefins 32 may be further separated or distilled in the olefin separation unit 40 to separate the stream's various components. In one embodiment, light end olefins 44 consisting of mainly $C_2$-$C_9$ compounds may be distilled into an overhead stream from the olefin separation unit 40. In certain embodiments, the light end olefins 44 are comprised of a majority of $C_3$-$C_8$ hydrocarbon compounds. In other embodiments, heavier olefins having higher carbon numbers may be separated overhead into the light end olefin stream 44 to assist in targeting a specific fuel composition. The light end olefins 44 may be recycled to the metathesis reactor 20, purged from the system for further processing and sold, or a combination of the two. In one embodiment, the light end olefins 44 may be partially purged from the system and partially recycled to the metathesis reactor 20. With regards to the other streams in the olefin separation unit 40, a heavier $C_{16+}$, $C_{18+}$, $C_{20+}$, $C_{22+}$, or $C_{24+}$ compound stream may be separated out as an olefin bottoms stream 46. This olefin bottoms stream 46 may be purged or recycled to the metathesis reactor 20 for further processing, or a combination of the two. In another embodiment, a center-cut olefin stream 42 may be separated out of the olefin distillation unit for further processing. The center-cut olefins 42 may be designed to target a selected carbon number range for a specific fuel composition. As a non-limiting example, a $C_5$-$C_{15}$ distribution may be targeted for further processing into a naphtha-type jet fuel. Alternatively, a $C_8$-$C_{16}$ distribution may be targeted for further processing into a kerosene-type jet fuel. In another embodiment, a $C_8$-$C_{25}$ distribution may be targeted for further processing into a diesel fuel.

In certain embodiments, the olefins 32 may be oligomerized to form poly-alpha-olefins (PAOs) or poly-internal-olefins (PIOs), mineral oil substitutes, and/or biodiesel fuel. The oligomerization reaction may take place after the distillation unit 30 or after the overhead olefin separation unit 40. In certain embodiments, byproducts from the oligomerization reactions may be recycled back to the metathesis reactor 20 for further processing.

As mentioned, in one embodiment, the olefins 32 from the separation unit 30 may be sent directly to the hydrogenation unit 50. In another embodiment, the center-cut olefins 42 from the overhead olefin separation unit 40 may be sent to the hydrogenation unit 50. Hydrogenation may be conducted according to any known method in the art for hydrogenating double bond-containing compounds such as the olefins 32 or center-cut olefins 42. In certain embodiments, in the hydrogenation unit 50, hydrogen gas 48 is reacted with the olefins 32 or center-cut olefins 42 in the presence of a hydrogenation catalyst to produce a hydrogenated product 52.

In some embodiments, the olefins are hydrogenated in the presence of a hydrogenation catalyst comprising nickel, copper, palladium, platinum, molybdenum, iron, ruthenium, osmium, rhodium, or iridium, individually or in combinations thereof. Useful catalyst may be heterogeneous or homogeneous. In some embodiments, the catalysts are supported nickel or sponge nickel type catalysts.

In some embodiments, the hydrogenation catalyst comprises nickel that has been chemically reduced with hydrogen to an active state (i.e., reduced nickel) provided on a support. The support may comprise porous silica (e.g., kieselguhr, infusorial, diatomaceous, or siliceous earth) or alumina. The catalysts are characterized by a high nickel surface area per gram of nickel.

Commercial examples of supported nickel hydrogenation catalysts include those available under the trade designations "NYSOFACT", "NYSOSEL", and "NI 5248 D" (from BASF Catalysts LLC, Iselin, N.J.). Additional supported nickel hydrogenation catalysts include those commercially available under the trade designations "PRICAT 9910", "PRICAT 9920", "PRICAT 9908", "PRICAT 9936" (from Johnson Matthey Catalysts, Ward Hill, Mass.).

The supported nickel catalysts may be of the type described in U.S. Pat. No. 3,351,566, U.S. Pat. No. 6,846,772, EP 0168091, and EP 0167201, incorporated by reference herein in their entireties. Hydrogenation may be carried out in a batch or in a continuous process and may be partial hydrogenation or complete hydrogenation. In certain embodiments, the temperature ranges from about 50° C. to about 350° C., about 100° C. to about 300° C., about 150° C. to about 250° C., or about 100° C. to about 150° C. The desired temperature may vary, for example, with hydrogen gas pressure. Typically, a higher gas pressure will require a lower temperature. Hydrogen gas is pumped into the reaction vessel to achieve a desired pressure of $H_2$ gas. In certain embodiments, the $H_2$ gas pressure ranges from about 15 psig (1 atm) to about 3000 psig (204.1 atm), about 15 psig (1 atm) to about 90 psig (6.1 atm), or about 100 psig (6.8 atm) to about 500 psig (34 atm). As the gas pressure increases, more specialized high-pressure processing equipment may be required. In certain embodiments, the reaction conditions are "mild," wherein the temperature is approximately between approximately 50° C. and approximately 100° C. and the $H_2$ gas pressure is less than approximately 100 psig. In other embodiments, the temperature is between about 100° C. and about 150° C., and the pressure is between about 100 psig (6.8 atm) and about 500 psig (34 atm). When the desired degree of hydrogenation is reached, the reaction mass is cooled to the desired filtration temperature.

The amount of hydrogenation catalyst is typically selected in view of a number of factors including, for example, the type of hydrogenation catalyst used, the amount of hydrogenation catalyst used, the degree of unsaturation in the material to be hydrogenated, the desired rate of hydrogenation, the desired degree of hydrogenation (e.g., as measure by iodine value (IV)), the purity of the reagent, and the $H_2$ gas pressure. In some embodiments, the hydrogenation catalyst is used in an amount of about 10 weight % or less, for example, about 5 weight % or less or about 1 weight % or less.

During hydrogenation, the carbon-carbon double bond containing compounds in the olefins are partially to fully saturated by the hydrogen gas 48. In one embodiment, the resulting hydrogenated product 52 includes hydrocarbons with a distribution centered between approximately $C_{10}$ and $C_{12}$ hydrocarbons for naphtha- and kerosene-type jet fuel compositions. In another embodiment, the distribution is centered between approximately $C_{16}$ and $C_{18}$ for a diesel fuel composition.

In certain embodiments, after hydrogenation, the hydrogenation catalyst may be removed from the hydrogenated product 52 using known techniques in the art, for example, by filtration. In some embodiments, the hydrogenation catalyst is removed using a plate and frame filter such as those commercially available from Sparkler Filters, Inc., Conroe Tex. In some embodiments, the filtration is performed with the assistance of pressure or a vacuum. In order to improve filtering performance, a filter aid may be used. A filter aid may be added to the product directly or it may be applied to the filter. Representative non-limiting examples of filtering aids include diatomaceous earth, silica, alumina, and carbon. Typically, the filtering aid is used in an amount of about 10 weight % or less, for example, about 5 weight % or less or about 1 weight % or less. Other filtering techniques and filtering aids also may be employed to remove the used hydrogenation catalyst. In other embodiments the hydrogenation catalyst is removed using centrifugation followed by decantation of the product.

In certain embodiments, based upon the quality of the hydrogenated product 52 produced in the hydrogenation unit 50, it may be preferable to isomerize the olefin hydrogenated product 52 to assist in targeting of desired fuel properties such as flash point, freeze point, energy density, cetane number, or end point distillation temperature, among other parameters. Isomerization reactions are well-known in the art, as described in U.S. Pat. Nos. 3,150,205; 4,210,771; 5,095,169; and 6,214,764, herein incorporated by reference in their entireities. In one embodiment, the isomerization reaction at this stage may also crack some of the $C_{15+}$ compounds remaining, which may further assist in producing a fuel composition having compounds within the desired carbon number range, such as 5 to 16 for a jet fuel composition.

In certain embodiments, the isomerization may occur concurrently with the hydrogenation step in the hydrogenation unit 50, thereby targeting a desired fuel product. In other embodiments, the isomerization step may occur before the hydrogenation step (i.e., the olefins 32 or center-cut olefins 42 may be isomerized before the hydrogenation unit 50). In yet other embodiments, it is possible that the isomerization step may be avoided or reduced in scope based upon the selection of low-molecular-weight olefin(s) 14 used in the metathesis reaction.

In certain embodiments, the hydrogenated product 52 comprises approximately 15-25 weight % $C_7$, approximately <5 weight % $C_8$, approximately 20-40 weight % $C_9$, approximately 20-40 weight % $C_{10}$, approximately <5 weight % $C_{11}$, approximately 15-25 weight % $C_{12}$, approximately <5 weight % $C_{13}$, approximately <5 weight % $C_{14}$, approximately <5 weight % $C_{15}$, approximately <1 weight % $C_{16}$, approximately <1 weight % $C_{17}$, and approximately <1 weight % $C_{18}+$. In certain embodiments, the hydrogenated product 52 comprises a heat of combustion of at least approximately 40, 41, 42, 43 or 44 MJ/kg (as measured by ASTM D3338). In certain embodiments, the hydrogenated product 52 contains less than approximately 1 mg sulfur per kg hydrogenated product (as measured by ASTM D5453). In other embodiments, the hydrogenated product 52 comprises a density of approximately 0.70-0.75 (as measured by ASTM D4052). In other embodiments, the hydrogenated product has a final boiling point of approximately 220-240° C. (as measured by ASTM D86).

The hydrogenated product 52 produced from the hydrogenation unit 50 may be used as a fuel composition, non-limiting examples of which include jet, kerosene, or diesel fuel. In certain embodiments, the hydrogenated product 52 may contain byproducts from the hydrogenation, isomerization, and/or metathesis reactions. As shown in FIG. 1, the hydrogenated product 52 may be further processed in a fuel composition separation unit 60, removing any remaining byproducts from the hydrogenated product 52, such as hydrogen gas, water, $C_2$-$C_9$ hydrocarbons, or $C_{15}+$ hydrocarbons, thereby producing a targeted fuel composition. In one embodiment, the hydrogenated product 52 may be separated into the desired fuel $C_9$-$C_{15}$ product 64, and a light-ends $C_2$-$C_9$ fraction 62 and/or a $C_{15}+$ heavy-ends fraction 66. Distillation may be used to separate the fractions. Alternatively, in other embodiments, such as for a naphtha- or kerosene-type jet fuel composition, the heavy ends fraction 66 can be separated from the desired fuel product 64 by cooling the hydrogenated product 52 to approximately −40° C., −47° C., or −65° C. and then removing the solid, heavy ends fraction 66 by techniques known in the art such as filtration, decantation, or centrifugation.

With regard to the esters 34 from the distillation unit 30, in certain embodiments, the esters 34 may be entirely withdrawn as an ester product stream 36 and processed further or sold for its own value, as shown in FIG. 1. As a non-limiting example, the esters 34 may comprise various triglycerides that could be used as a lubricant. Based upon the quality of separation between olefins and esters, the esters 34 may comprise some heavier olefin components carried with the triglycerides. In other embodiments, the esters 34 may be further processed in a biorefinery or another chemical or fuel processing unit known in the art, thereby producing various products such as biodiesel or specialty chemicals that have higher value than that of the triglycerides, for example. Alternatively, in certain embodiments, the esters 34 may be partially withdrawn from the system and sold, with the remainder further processed in the biorefinery or another chemical or fuel processing unit known in the art.

In certain embodiments, the ester stream 34 is sent to a transesterification unit 70. Within the transesterification unit 70, the esters 34 are reacted with at least one alcohol 38 in the presence of a transesterification catalyst. In certain embodiments, the alcohol comprises methanol and/or ethanol. In one embodiment, the transesterification reaction is conducted at approximately 60-70° C. and approximately 1 atm. In certain embodiments, the transesterification catalyst is a homogeneous sodium methoxide catalyst. Varying amounts of catalyst may be used in the reaction, and, in certain embodiments, the transesterification catalyst is present in the amount of approximately 0.5-1.0 weight % of the esters 34.

The transesterification reaction may produce transesterified products 72 including saturated and/or unsaturated fatty acid methyl esters ("FAME"), glycerin, methanol, and/or free fatty acids. In certain embodiments, the transesterified products 72, or a fraction thereof, may comprise a source for biodiesel. In certain embodiments, the transesterified products 72 comprise 9DA esters, 9UDA esters, and/or 9DDA esters. Non-limiting examples of 9DA esters, 9UDA esters and 9DDA esters include methyl 9-decenoate ("9-DAME"), methyl 9-undecenoate ("9-UDAME"), and methyl 9-dodecenoate ("9-DDAME"), respectively. As a non-limiting example, in a transesterification reaction, a 9DA moiety of a metathesized glyceride is removed from the glycerol backbone to form a 9DA ester.

In another embodiment, a glycerin alcohol may be used in the reaction with a glyceride stream. This reaction may produce monoglycerides and/or diglycerides.

In certain embodiments, the transesterified products 72 from the transesterification unit 70 can be sent to a liquid-liquid separation unit, wherein the transesterified products 72 (i.e., FAME, free fatty acids, and/or alcohols) are separated from glycerin. Additionally, in certain embodiments, the glycerin byproduct stream may be further processed in a secondary separation unit, wherein the glycerin is removed and any remaining alcohols are recycled back to the transesterification unit 70 for further processing.

In one embodiment, the transesterified products 72 are further processed in a water-washing unit. In this unit, the transesterified products undergo a liquid-liquid extraction when washed with water. Excess alcohol, water, and glycerin are removed from the transesterified products 72. In another embodiment, the water-washing step is followed by a drying unit in which excess water is further removed from the desired mixture of esters (i.e., specialty chemicals). Such specialty chemicals include non-limiting examples such as 9DA, 9UDA, and/or 9DDA, alkali metal salts and alkaline earth metal salts of the preceding, individually or in combinations thereof.

In one embodiment, the specialty chemical (e.g., 9DA) may be further processed in an oligomerization reaction to form a lactone, which may serve as a precursor to a surfactant.

In certain embodiments, the transesterifed products 72 from the transesterification unit 70 or specialty chemicals from the water-washing unit or drying unit are sent to an ester distillation column 80 for further separation of various individual or groups of compounds, as shown in FIG. 1. This separation may include, but is not limited to, the separation of 9DA esters, 9UDA esters, and/or 9DDA esters. In one embodiment, the 9DA ester 82 may be distilled or individually separated from the remaining mixture 84 of transesterified products or specialty chemicals. In certain process conditions, the 9DA ester 82 should be the lightest component in the transesterified product or specialty chemical stream, and come out at the top of the ester distillation column 80. In another embodiment, the remaining mixture 84, or heavier components, of the transesterified products or specialty chemicals may be separated off the bottom end of the column. In certain embodiments, this bottoms stream 84 may potentially be sold as biodiesel.

The 9DA esters, 9UDA esters, and/or 9DDA esters may be further processed after the distillation step in the ester distillation column. In one embodiment, under known operating conditions, the 9DA ester, 9UDA ester, and/or 9DDA ester may then undergo a hydrolysis reaction with water to form 9DA, 9UDA, and/or 9DDA, alkali metal salts and alkaline earth metal salts of the preceding, individually or in combinations thereof.

In certain embodiments, the fatty acid methyl esters from the transesterified products 72 may be reacted with each other to form other specialty chemicals such as dimers.

Figure 2:
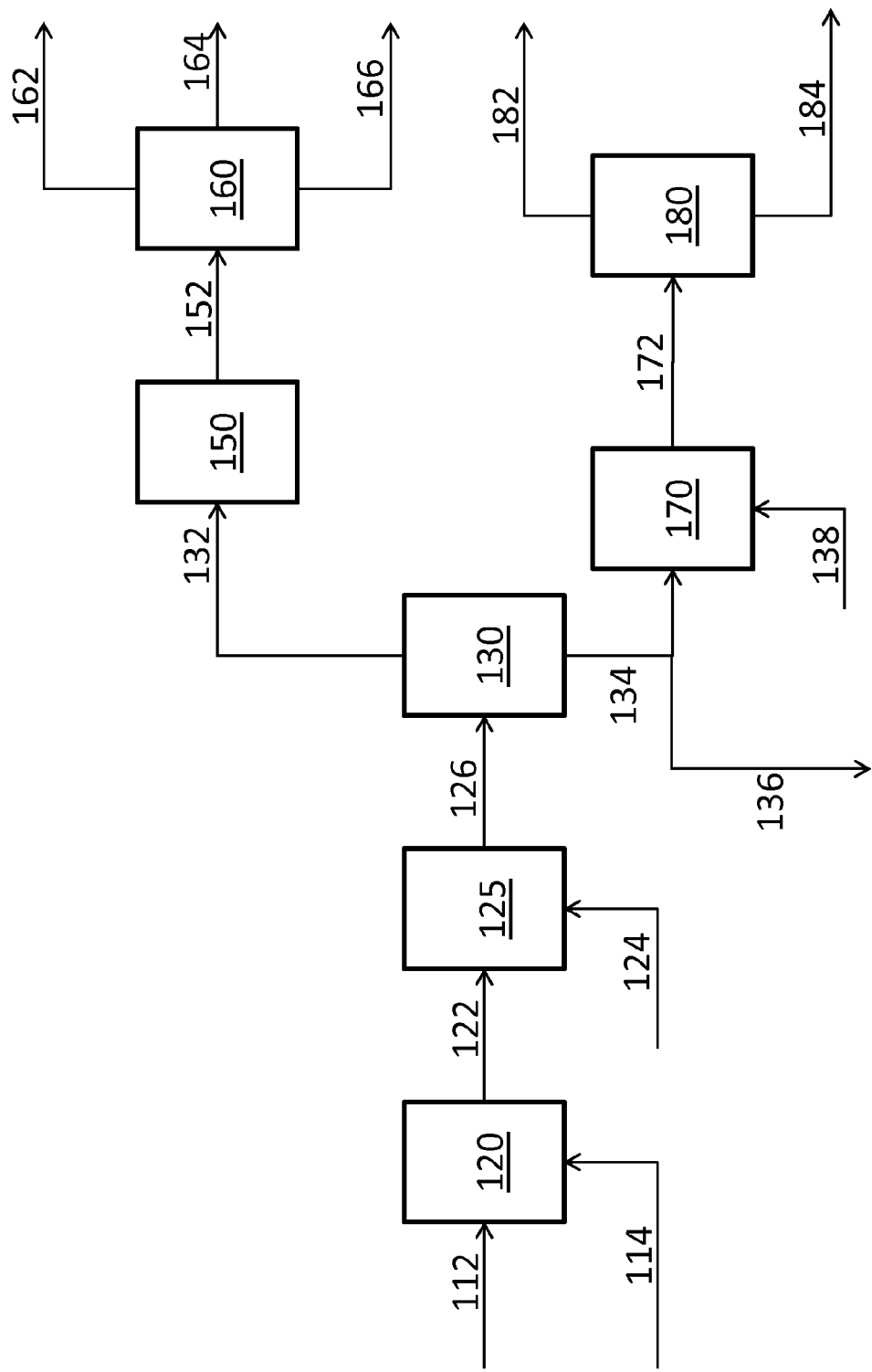
FIG. 2 is a schematic diagram of a second embodiment of a process to produce a fuel composition and a transesterified product from a natural oil.

FIG. 2 represents another embodiment for processing the natural oil into fuel compositions and specialty chemicals. As described above, the natural oil feedstock and/or low-molecular-weight olefin in FIG. 2 may undergo a pretreatment step prior to the metathesis reaction. In FIG. 2, the natural oil feedstock 112 is reacted with itself, or combined with a low-molecular-weight olefin 114 in a metathesis reactor 120 in the presence of a metathesis catalyst. In certain embodiments, in the presence of a metathesis catalyst, the natural oil 112 undergoes a self-metathesis reaction with itself. In other embodiments, in the presence of the metathesis catalyst, the natural oil 112 undergoes a cross-metathesis reaction with the low-molecular-weight olefin 114. In certain embodiments, the natural oil 112 undergoes both self- and cross-metathesis reactions in parallel metathesis reactors. The self-metathesis and/or cross-metathesis reaction form a metathesized product 122 wherein the metathesized product 122 comprises olefins 132 and esters 134.

In certain embodiments, the low-molecular-weight olefin 114 is in the $C_2$ to $C_6$ range. As a non-limiting example, in one embodiment, the low-molecular-weight olefin 114 may comprise at least one of the following: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. In another embodiment, the low-molecular-weight olefin 114 comprises at least one of styrene and vinyl cyclohexane. In another embodiment, the low-molecular-weight olefin 114 may comprise at least one of ethylene, propylene, 1-butene, 2-butene, and isobutene. In another embodiment, the low-molecular-weight olefin 114 comprises at least one alpha-olefin or terminal olefin in the $C_2$ to $C_{10}$ range.

In another embodiment, the low-molecular-weight olefin 114 comprises at least one branched low-molecular-weight olefin in the $C_4$ to $C_{10}$ range. Non-limiting examples of branched low-molecular-weight olefins include isobutene, 3-methyl-1-butene, 2-methyl-3-pentene, and 2,2-dimethyl-3-pentene. In certain embodiments, the branched low-molecular-weight olefins may help achieve the desired performance properties for the fuel composition, such as jet, kerosene, or diesel fuel.

As noted, it is possible to use a mixture of various linear or branched low-molecular-weight olefins in the reaction to achieve the desired metathesis product distribution. In one embodiment, a mixture of butenes (1-butene, 2-butene, and isobutene) may be employed as the low-molecular-weight olefin 114.

In certain embodiments, recycled streams from downstream separation units may be introduced to the metathesis reactor 120 in addition to the natural oil 112 and, in some embodiments, the low-molecular-weight olefin 114 to improve the yield of the targeted fuel composition and/or targeted transesterification products.

After the metathesis unit 120 and before the hydrogenation unit 125, in certain embodiments, the metathesized product 122 may be introduced to an adsorbent bed to facilitate the separation of the metathesized product 122 from the metathesis catalyst. In one embodiment, the adsorbent is a clay. The clay will adsorb the metathesis catalyst, and after a filtration step, the metathesized product 122 can be sent to the hydrogenation unit 125 for further processing. In another embodiment, the adsorbent is a water soluble phosphine reagent such as tris hydroxymethyl phosphine (THMP). Catalyst may be separated from the reaction mixture with a water soluble phosphine through known liquid-liquid extraction mechanisms by decanting the aqueous phase from the organic phase. In other embodiments, addition of a reactant to deactivate or extract the catalyst might be used.

As shown in FIG. 2, the metathesis product 122 is sent to a hydrogenation unit 125, wherein the carbon-carbon double bonds in the olefins and esters are partially to fully saturated with hydrogen gas 124. As described above, hydrogenation may be conducted according to any known method in the art for hydrogenating double bond-containing compounds such as the olefins and esters present in the metathesis product 122. In certain embodiments, in the hydrogenation unit 125, hydrogen gas 124 is reacted with the metathesis product 122 in the presence of a hydrogenation catalyst to produce a hydrogenated product 126 comprising partially to fully hydrogenated paraffins/olefins and partially to fully hydrogenated esters.

Typical hydrogenation catalysts have been already described with reference to embodiments in FIG. 1. Reaction conditions have also been described. In certain embodiments, the temperature ranges from about 50° C. to about 350° C., about 100° C. to about 300° C., about 150° C. to about 250° C., or about 50° C. to about 150° C. The desired temperature may vary, for example, with hydrogen gas pressure. Typically, a higher gas pressure might allow the use of a lower reaction temperature. Hydrogen gas is pumped into the reaction vessel to achieve a desired pressure of $H_2$ gas. In certain embodiments, the $H_2$ gas pressure ranges from about 15 psig (1 atm) to about 3000 psig (204.1 atm), or about 15 psig (1 atm) to about 500 psig (34 atm). In certain embodiments, the reaction conditions are "mild," wherein the temperature is approximately between approximately 50° C. and approximately 150° C. and the $H_2$ gas pressure is less than approximately 400 psig. When the desired degree of hydrogenation is reached, the reaction mass is cooled to the desired filtration temperature.

During hydrogenation, the carbon-carbon double bonds are partially to fully saturated by the hydrogen gas 124. In one embodiment, the olefins in the metathesis product 122 are reacted with hydrogen to form a fuel composition comprising only or mostly paraffins. Additionally, the esters from the metathesis product are fully or nearly fully saturated in the hydrogenation unit 125. In another embodiment, the resulting hydrogenated product 126 includes only partially saturated paraffins/olefins and partially saturated esters.

In FIG. 2, the hydrogenated product 126 is sent to a separation unit 130 to separate the product into at least two product streams. In one embodiment, the hydrogenated product 126 is sent to the separation unit 130, or distillation column, to separate the partially to fully saturated paraffins/olefins, or fuel composition 132, from the partially to fully saturated esters 134. In another embodiment, a byproduct stream comprising $C_7$'s and cyclohexadiene may be removed in a sidestream from the separation unit 130. In certain embodiments, the fuel composition 132 may comprise hydrocarbons with carbon numbers up to 24. In one embodiment, the fuel composition 132 consists essentially of saturated hydrocarbons.

In certain embodiments, the esters 134 may comprise metathesized, partially to fully hydrogenated glycerides. In other words, the lighter end paraffins/olefins 132 are preferably separated or distilled overhead for processing into fuel compositions, while the esters 134, comprised mostly of compounds having carboxylic acid/ester functionality, are drawn as a bottoms stream. Based on the quality of the separation, it is possible for some ester compounds to be carried into the overhead paraffin/olefin stream 132, and it is also possible for some heavier paraffin/olefin hydrocarbons to be carried into the ester stream 134.

In certain embodiments, it may be preferable to isomerize the fuel composition 132 to improve the quality of the product stream and target the desired fuel properties such as flash point, freeze point, energy density, cetane number, or end point distillation temperature, among other parameters. Isomerization reactions are well-known in the art, as described in U.S. Pat. Nos. 3,150,205; 4,210,771; 5,095,169; and 6,214,764, herein incorporated by reference in their entireties. In one embodiment, as shown in FIG. 2, the fuel composition 132 is sent to an isomerization reaction unit 150 wherein an isomerized fuel composition 152 is produced. Under typical reaction conditions, the isomerization reaction at this stage may also crack some of the compounds present in stream 132, which may further assist in producing an improved fuel composition having compounds within the desired carbon number range, such as 5 to 16 for a jet fuel composition.

In certain embodiments, the fuel composition 132 or isomerized fuel composition 152 comprises approximately 15-25 weight % $C_7$, approximately <5 weight % $C_8$, approximately 20-40 weight % $C_9$, approximately 20-40 weight % $C_{10}$, approximately <5 weight % $C_{11}$, approximately 15-25 weight % $C_{12}$, approximately <5 weight % $C_{13}$, approximately <5 weight % $C_{14}$, approximately <5 weight % $C_{15}$, approximately <1 weight % $C_{16}$, approximately <1 weight % $C_{17}$, and approximately <1 weight % $C_{18}+$. In certain embodiments, the fuel composition 132 or isomerized fuel composition 152 comprises a heat of combustion of at least approximately 40, 41, 42, 43 or 44 MJ/kg (as measured by ASTM D3338). In certain embodiments, the fuel composition 132 or isomerized fuel composition 152 contains less than approximately 1 mg sulfur per kg fuel composition (as measured by ASTM D5453). In other embodiments, the fuel composition 132 or isomerized fuel composition 152 comprises a density of approximately 0.70-0.75 (as measured by ASTM D4052). In other embodiments, the fuel composition 132 or isomerized fuel composition 152 has a final boiling point of approximately 220-240° C. (as measured by ASTM D86).

The fuel composition 132 or the isomerized fuel composition 152 may be used as jet, kerosene, or diesel fuel, depending on the fuel's characteristics. In certain embodiments, the fuel composition may contain byproducts from the hydrogenation, isomerization, and/or metathesis reactions. The fuel composition 132 or isomerized fuel composition 152 may be further processed in a fuel composition separation unit 160 as shown in FIG. 2. The separation unit 160 may be operated to remove any remaining byproducts from the mixture, such as hydrogen gas, water, $C_2$-$C_9$ hydrocarbons, or $C_{15}+$ hydrocarbons, thereby producing a desired fuel product 164. In one embodiment, the mixture may be separated into the desired fuel $C_9$-$C_{15}$ product 164, and a light-ends $C_2$-$C_9$ (or $C_3$-$C_8$) fraction 162 and/or a $C_{18}+$ heavy-ends fraction 166. Distillation may be used to separate the fractions. Alternatively, in other embodiments, such as for a naphtha- or kerosene-type jet fuel composition, the heavy ends fraction 166 can be separated from the desired fuel product 164 by cooling the paraffins/olefins to approximately −40° C., −47° C., or −65° C. and then removing the solid, heavy ends fraction 166 by techniques known in the art such as filtration, decantation, or centrifugation.

With regard to the partially to fully saturated esters 134 from the separation unit 130, in certain embodiments, the esters 134 may be entirely withdrawn as a partially to fully hydrogenated ester product stream 136 and processed further or sold for its own value, as shown in FIG. 2. As a non-limiting example, the esters 134 may comprise various partially to fully saturated triglycerides that could be used as a lubricant. Based upon the quality of separation between the paraffins/olefins (fuel composition 132) and the esters, the esters 134 may comprise some heavier paraffin and olefin components carried with the triglycerides. In other embodiments, the esters 134 may be further processed in a biorefinery or another chemical or fuel processing unit known in the art, thereby producing various products such as biodiesel or specialty chemicals that have higher value than that of the triglycerides, for example. Alternatively, the esters 134 may be partially withdrawn from the system and sold, with the remainder further processed in the biorefinery or another chemical or fuel processing unit known in the art.

In certain embodiments, the ester stream 134 is sent to a transesterification unit 170. Within the transesterification unit 170, the esters 134 are reacted with at least one alcohol 138 in the presence of a transesterification catalyst. In certain embodiments, the alcohol comprises methanol and/or ethanol. In one embodiment, the transesterification reaction is conducted at approximately 60-70° C. and 1 atm. In certain embodiments, the transesterification catalyst is a homogeneous sodium methoxide catalyst. Varying amounts of catalyst may be used in the reaction, and, in certain embodiments, the transesterification catalyst is present in the amount of approximately 0.5-1.0 weight % of the esters 134.

The transesterification reaction may produce transesterified products 172 including saturated and/or unsaturated fatty acid methyl esters ("FAME"), glycerin, methanol, and/or free fatty acids. In certain embodiments, the transesterified products 172, or a fraction thereof, may comprise a source for biodiesel. In certain embodiments, the transesterified products 172 comprise decenoic acid esters, decanoic acid esters, undecenoic acid esters, undecanoic acid esters, dodecenoic acid esters, and/or dodecaonic acid esters. In one embodiment, in a transesterification reaction, a decanoic acid moiety of a metathesized glyceride is removed from the glycerol backbone to form a decanoic acid ester. In another embodiment, a decenoic acid moiety of a metathesized glyceride is removed from the glycerol backbone to form a decenoic acid ester.

In another embodiment, a glycerin alcohol may be used in the reaction with a triglyceride stream 134. This reaction may produce monoglycerides and/or diglycerides.

In certain embodiments, the transesterified products 172 from the transesterification unit 170 can be sent to a liquid-liquid separation unit, wherein the transesterified products 172 (i.e., FAME, free fatty acids, and/or alcohols) are separated from glycerin. Additionally, in certain embodiments, the glycerin byproduct stream may be further processed in a secondary separation unit, wherein the glycerin is removed and any remaining alcohols are recycled back to the transesterification unit 170 for further processing.

In one embodiment, the transesterified products 172 are further processed in a water-washing unit. In this unit, the transesterified products undergo a liquid-liquid extraction when washed with water. Excess alcohol, water, and glycerin are removed from the transesterified products 172. In another embodiment, the water-washing step is followed by a drying unit in which excess water is further removed from the desired mixture of esters (i.e., specialty chemicals). Such hydrogenated specialty chemicals include non-limiting examples such as decenoic acid, decanoic acid, undecenoic acid, undecanoic acid, dodecenoic acid, dodecanoic acid, and mixtures thereof.

As shown in FIG. 2, the transesterifed products 172 from the transesterification unit 170 or specialty chemicals from the water-washing unit or drying unit may be sent to an ester distillation column 180 for further separation of various individual or groups of compounds. This separation may include, but is not limited to, the separation of decenoic acid esters, decanoic acid esters, undecenoic acid esters, undecanoic acid esters, dodecenoic acid esters, and/or dodecanoic acid esters. In one embodiment, a decanoic acid ester or decenoic acid ester 182 may be distilled or individually separated from the remaining mixture 184 of transesterified products or specialty chemicals. In certain process conditions, the decanoic acid ester or decenoic acid ester 182 should be the lightest component in the transesterified product or specialty chemical stream, and come out at the top of the ester distillation column 180. In another embodiment, the remaining mixture 184, or heavier components, of the transesterified products or specialty chemicals may be separated off the bottom end of the column. In certain embodiments, this bottoms stream 184 may potentially be sold as biodiesel.

The decenoic acid esters, decanoic acid esters, undecenoic acid esters, undecanoic acid esters, dodecenoic acid esters, and/or dodecanoic acid esters may be further processed after the distillation step in the ester distillation column. In one embodiment, under known operating conditions, the decenoic acid ester, decanoic acid ester, undecenoic acid ester, undecanoic acid ester, dodecenoic acid ester, and/or dodecanoic acid ester may then undergo a hydrolysis reaction with water to form decenoic acid, decanoic acid, undecenoic acid undecanoic acid, dodecenoic acid, and/or dodecanoic acid.

As noted, the self-metathesis of the natural oil or the cross-metathesis between the natural oil and low-molecular-weight olefin occurs in the presence of a metathesis catalyst. As stated previously, the term "metathesis catalyst" includes any catalyst or catalyst system that catalyzes a metathesis reaction. Any known or future-developed metathesis catalyst may be used, individually or in combination with one or more additional catalysts. Non-limiting exemplary metathesis catalysts and process conditions are described in PCT/US2008/009635, pp. 18-47, incorporated by reference herein. A number of the metathesis catalysts as shown are manufactured by Materia, Inc. (Pasadena, Calif.).

The metathesis process can be conducted under any conditions adequate to produce the desired metathesis products. For example, stoichiometry, atmosphere, solvent, temperature, and pressure can be selected by one skilled in the art to produce a desired product and to minimize undesirable byproducts. The metathesis process may be conducted under an inert atmosphere. Similarly, if a reagent is supplied as a gas, an inert gaseous diluent can be used. The inert atmosphere or inert gaseous diluent typically is an inert gas, meaning that the gas does not interact with the metathesis catalyst to substantially impede catalysis. For example, particular inert gases are selected from the group consisting of helium, neon, argon, nitrogen, individually or in combinations thereof.

In certain embodiments, the metathesis catalyst is dissolved in a solvent prior to conducting the metathesis reaction. In certain embodiments, the solvent chosen may be selected to be substantially inert with respect to the metathesis catalyst. For example, substantially inert solvents include, without limitation, aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc. In one particular embodiment, the solvent comprises toluene.

The metathesis reaction temperature may be a rate-controlling variable where the temperature is selected to provide a desired product at an acceptable rate. In certain embodiments, the metathesis reaction temperature is greater than about −40° C., greater than about −20° C., greater than about 0° C., or greater than about 10° C. In certain embodiments, the metathesis reaction temperature is less than about 150° C., or less than about 120° C. In one embodiment, the metathesis reaction temperature is between about 10° C. and about 120° C.

The metathesis reaction can be run under any desired pressure. Typically, it will be desirable to maintain a total pressure that is high enough to keep the cross-metathesis reagent in solution. Therefore, as the molecular weight of the cross-metathesis reagent increases, the lower pressure range typically decreases since the boiling point of the cross-metathesis reagent increases. The total pressure may be selected to be greater than about 0.1 atm (10 kPa), in some embodiments greater than about 0.3 atm (30 kPa), or greater than about 1 atm (100 kPa). Typically, the reaction pressure is no more than about 70 atm (7000 kPa), in some embodiments no more than about 30 atm (3000 kPa). A non-limiting exemplary pressure range for the metathesis reaction is from about 1 atm (100 kPa) to about 30 atm (3000 kPa).

While the invention as described may have modifications and alternative forms, various embodiments thereof have been described in detail. It should be understood, however, that the description herein of these various embodiments is not intended to limit the invention, but on the contrary, the intention is to cover all modifications, equivalents, and alternatives falling within the spirit and scope of the invention as defined by the claims. Further, while the invention will also be described with reference to the following non-limiting examples, it will be understood, of course, that the invention is not limited thereto since modifications may be made by those skilled in the art, particularly in light of the foregoing teachings.

EXAMPLES

Example 1

A clean, dry, stainless steel jacketed 5-gal. Parr reactor vessel equipped with a dip tube, overhead stirrer, internal cooling/heated coils, temperature probe, sampling valve, and headspace gas release valve was purged with argon to 15 psig. Soybean oil (SBO, 2.5 kg, 2.9 mol, Costco, MWn=864.4 g/mol, 85 weight % unsaturation as determined by GC, 1 hour argon sparged in 5-gal container) was added into the Parr reactor. The Parr reactor was sealed and the SBO was purged with argon for 2 hours while cooling to 10° C. After 2 hours, the reactor was vented until the internal pressure reached 10 psig. The dip tube valve on the reactor was connected to a 1-butene cylinder (Airgas, CP grade, 33 psig headspace pressure, >99 weight %) and re-pressurized to 15 psig of 1-butene. The reactor was vented again to 10 psig to remove residual argon in the headspace. The SBO was stirred at 350 rpm and 9-15° C. under 18-28 psig 1-butene until 3 mol 1-butene per SBO olefin bond was transferred into the reactor (approximately 2.2 kg 1-butene over approximately 4-5 hours). A toluene solution of [1,3-Bis-(2,4,6-trimethylphenyl)-2-imidazolidinylidene]dichlororuthenium(3-methyl-2-butenylidene)(tricyclohexylphosphine) (C827, Materia) was prepared in Fischer-Porter pressure vessel by dissolving 130 mg catalyst in 30 grams of toluene as a catalyst carrier (10 mol ppm per olefin bond of SBO) and was added to the reactor via the reactor dip tube by pressurizing the headspace inside the Fischer-Porter vessel to 50-60 psig with argon. The Fischer-Porter vessel and dip tube were rinsed with an additional 30 g toluene. The reaction mixture was stirred for 2.0 hours at 60° C. The reaction mixture was allowed to cool to ambient temperature while the gases in the headspace were vented. After the pressure was released, the reaction mixture was transferred to a 3-neck round bottom flask containing 58 g bleaching clay (2% w/w SBO, Pure Flow B80 CG) and a magnetic stir bar. The reaction mixture was treated by stirring at 85° C. under argon. After 2 hours, during which time any remaining 1-butene was allowed to vent, the reaction mixture was allowed to cool to 40° C. and filtered through a fritted glass filter. An aliquot of the product mixture was found by gas chromatographic analysis (following transesterification with 1% w/w NaOMe in methanol at 60° C.). to contain approximately 22 weight % methyl 9-decenoate, approximately 16 weight % methyl 9-dodecenoate, approximately 3 weight % dimethyl 9-octadecenedioate, and approximately 3 weight % methyl 9-octadecenoate (by gc). These results compare favorably with the calculated yields at equilibrium of 23.4 wt % methyl 9-decenoate, 17.9 wt % methyl 9-dodecenoate, 3.7 wt % dimethyl 9-octadecenedioate, and 1.8 wt % methyl 9-octadecenoate.

Example 2

By the general procedures described in example 1, a reaction was performed using 1.73 kg SBO and 3 mol 1-butene/SBO double bond. An aliquot of the product mixture was found by gas chromatographic analysis following transesterification with 1% w/w NaOMe in methanol at 60° C. to contain approximately 24 weight % methyl 9-decenoate, approximately 18 weight % methyl 9-dodecenoate, approximately 2 weight % dimethyl 9-octadecenedioate, and approximately 2 weight % methyl 9-octadecenoate (as determined by gc).

Example 3

By the general procedures described in example 1, a reaction was performed using 1.75 kg SBO and 3 mol 1-butene/SBO double bond. An aliquot of the product mixture was found by gas chromatographic analysis following transesterification with 1% w/w NaOMe in methanol at 60° C. to contain approximately 24 weight % methyl 9-decenoate, approximately 17 weight % methyl 9-dodecenoate, approximately 3 weight % dimethyl 9-octadecenedioate, and approximately 2 weight % methyl 9-octadecenoate (as determined by gc).

Example 4

By the general procedures described in example 1, a reaction was performed using 2.2 kg SBO, 3 mol 1-butene/SBO double bond, and the 60 g of toluene used to transfer the catalyst was replaced with SBO. An aliquot of the product mixture was found by gas chromatographic analysis following transesterification with 1% w/w NaOMe in methanol at 60° C. to contain approximately 25 weight % methyl 9-decenoate, approximately 18 weight % methyl 9-dodecenoate, approximately 3 weight % dimethyl 9-octadecenedioate, and approximately 1 weight % methyl 9-octadecenoate (as determined by gc).

Example 5

A 12-liter, 3-neck, glass round bottom flask that was equipped with a magnetic stir bar, heating mantle, and temperature controller was charged with 8.42 kg of the combined reaction products from examples 1-4. A cooling condenser with a vacuum inlet was attached to the middle neck of the flask and a receiving flask was connected to the condenser. Hydrocarbon olefins were removed from the reaction product by vacuum distillation over the follow range of conditions: 22-130° C. pot temperature, 19-70° C. distillation head temperature, and 2000-160 μtorr pressure. The weight of material remaining after the volatile hydrocarbons were removed was 5.34 kg. An aliquot of the non-volatile product mixture was found by gas chromatographic analysis following transesterification with 1% w/w NaOMe in methanol at 60° C. to contain approximately 32 weight % methyl 9-decenoate, approximately 23 weight % methyl 9-dodecenoate, approximately 4 weight % dimethyl 9-octadecenedioate, and approximately 5 weight % methyl 9-octadecenoate (as determined by gc).

Example 6

A 12-liter, 3-neck round bottom flask that was fitted with a magnetic stir bar, condenser, heating mantle, temperature probe, and gas adapter was charged with 4 liters of 1% w/w NaOMe in MeOH and 5.34 kg of the non-volatile product mixture produced in example 5. The resulting light yellow heterogeneous mixture was stirred at 60° C. After about an hour, the mixture turned a homogeneous orange color (detected pH=11.) After a total reaction time of 2 hours, the mixture was cooled to ambient temperature and two layers were observed. The organic phase was washed twice with 3 L of 50% (v/v) aqueous MeOH, separated, and neutralized by washing with glacial HOAc in MeOH (1 mol HOAc/mol NaOMe) to a detected pH of 6.5, yielding 5.03 kg.

Example 7

A glass, 12 L, 3-neck round bottom flask fitted with a magnetic stirrer, packed column, and temperature controller was charged with the methyl ester mixture (5.03 kg) produced in example 6 and placed in the heating mantle. The column attached to the flask was a 2-inch×36-inch glass column containing 0.16" Pro-Pak™ stainless steel saddles. The distillation column was attached to a fractional distillation head to which a 1 L pre-weighed round bottom flask was fitted for collecting the distillation fractions. The distillation was carried out under vacuum at 100-120 μtorr. A reflux ratio of 1:3 was used for isolating both methyl 9-decenoate (9-DAME) and methyl 9-dodecenoate (9-DDAME). A reflux ratio of 1:3 referred to 1 drop collected for every 3 drops sent back to the distillation column. The samples collected during the distillation, the vacuum distillation conditions, and the 9-DAME and 9-DDAME content of the fractions, as determined by gc, are shown in Table 1. Combining fractions 2-7 yielded 1.46 kg methyl 9-decenoate with 99.7% purity. After collecting fraction 16, 2.50 kg of material remained in the distillation pot: it was found by gc to contain approximately 14 weight % 9-DDAME, approximately 42 weight % methyl palmitate, and approximately 12 weight % methyl stearate.

TABLE 1

| Distillation Fractions # | Head temp. (° C.) | Pot temp. (° C.) | Vacuum (µtorr) | Weight (g) | 9-DAME (wt %) | 9-DDAME (wt %) |
|---|---|---|---|---|---|---|
| 1 | 40-47 | 104-106 | 110 | 6.8 | 80 | 0 |
| 2 | 45-46 | 106 | 110 | 32.4 | 99 | 0 |
| 3 | 47-48 | 105-110 | 120 | 223.6 | 99 | 0 |
| 4 | 49-50 | 110-112 | 120 | 283 | 99 | 0 |
| 5 | 50 | 106 | 110 | 555 | 99 | 0 |
| 6 | 50 | 108 | 110 | 264 | 99 | 0 |
| 7 | 50 | 112 | 110 | 171 | 99 | 0 |
| 8 | 51 | 114 | 110 | 76 | 97 | 1 |
| 9 | 65-70 | 126-128 | 110 | 87 | 47 | 23 |
| 10 | 74 | 130-131 | 110 | 64 | 0 | 75 |
| 11 | 75 | 133 | 110 | 52.3 | 0 | 74 |
| 12 | 76 | 135-136 | 110 | 38 | 0 | 79 |
| 13 | 76 | 136-138 | 100 | 52.4 | 0 | 90 |
| 14 | 76 | 138-139 | 100 | 25.5 | 0 | 85 |
| 15 | 76-77 | 140 | 110 | 123 | 0 | 98 |
| 16 | 78 | 140 | 100 | 426 | 0 | 100 |

Example 8

A reaction was performed by the general procedures described in example 1 with the following changes: 2.2 kg SBO, 7 mol propene/mol SBO double bond, and 200 mg [1,3-Bis-(2,4,6-trimethylphenyl)-2-imidazolidinylidene] dichlororuthenium(benzylidene)(tricyclohexyl-phosphine) [C848 catalyst, Materia Inc., Pasadena, Calif., USA, 90 ppm (w/w) vs. SBO] at a reaction temperature of 40° C. were used. The catalyst removal step using bleaching clay also was replaced by the following: after venting excess propene, the reaction mixture was transferred into a 3-neck round bottom flask to which tris(hydroxymethyl)phosphine (THMP, 1.0 M in isopropanol, 50 mol THMP/mol C848) was added. The resulting hazy yellow mixture was stirred for 20 hours at 60° C., transferred to a 6-L separatory funnel and extracted with 2×2.5 L deionized H$_2$O. The organic layer was separated and dried over anhydrous Na$_2$SO$_4$ for 4 hours, then filtered through a fritted glass filter containing a bed of silica gel.

Example 9

A reaction was performed by the general procedures described in example 8, except that 3.6 kg SBO and 320 mg C848 catalyst were used. Following catalyst removal, the reaction product from example 9 was combined with that from example 8, yielding 5.12 kg of material. An aliquot of the combined product mixture was found by gas chromatographic analysis following transesterification with 1% w/w NaOMe in methanol at 60° C. to contain approximately 34 weight % methyl 9-decenoate, approximately 13 weight % methyl 9-undecenoate, <1 weight % dimethyl 9-octadecenedioate, and <1 weight % methyl 9-octadecenoate (as determined by gc).

Hydrocarbon olefins were removed from the 5.12 kg of combined reaction product described above by vacuum distillation by the general procedure described in example 5. The weight of material remaining after the volatile olefins were removed was 4.0 kg. An aliquot of the non-volatile product mixture was found by gas chromatographic analysis following transesterification with 1% w/w NaOMe in methanol at 60° C. to contain approximately 46 weight % methyl 9-decenoate, approximately 18 weight % methyl 9-undecenoate, approximately 2 weight % dimethyl 9-octadecenedioate, and approximately 1 weight % methyl 9-octadecenoate (as determined by gc).

Example 10

Two reactions were performed by the general procedures described in example 8, except that for each reaction, 3.1 kg SBO and 280 mg C848 catalyst were used. Following catalyst removal, the reaction products from the two preparations were combined, yielding 5.28 kg of material. An aliquot of the combined product mixture was found by gas chromatographic analysis following transesterification with 1% w/w NaOMe in methanol at 60° C. to contain approximately 40 weight % methyl 9-decenoate, approximately 13 weight % methyl 9-undecenoate, approximately 2 weight % dimethyl 9-octadecenedioate, and approximately 1 weight % methyl 9-octadecenoate (as determined by gc).

Hydrocarbon olefins were removed from the 5.28 kg of combined reaction product by vacuum distillation by the general procedure described in example 5. The weight of material remaining after the volatile olefins were removed was 4.02 kg. An aliquot of the non-volatile product mixture was found by gas chromatographic analysis following transesterification with 1% w/w NaOMe in methanol at 60° C. to contain approximately 49 weight % methyl 9-decenoate, approximately 16 weight % methyl 9-undecenoate, approximately 2 weight % dimethyl 9-octadecenedioate, and approximately 3 weight % methyl 9-octadecenoate (as determined by gc).

Example 11

By the general procedures described in example 10, two metathesis reactions were performed using SBO, 7 mol cis-2-butene/mol SBO double bond, and 220 mg C848 catalyst/kg SBO. Following catalyst removal, the reaction products from the two preparations were combined, yielding 12.2 kg of material. An aliquot of the combined product mixture was found by gas chromatographic analysis following transesterification with 1% w/w NaOMe in methanol at 60° C. to contain approximately 49 weight % methyl 9-undecenoate, approximately 2 weight % dimethyl 9-octadecenedioate, and approximately 1 weight % methyl 9-octadecenoate (as determined by gc).

Hydrocarbon olefins were removed from the 12.2 kg of combined reaction product by vacuum distillation by the general procedure described in example 5. The weight of material remaining after the volatile olefins were removed was 7.0 kg. An aliquot of the non-volatile product mixture was found by gas chromatographic analysis following transesterification with 1% w/w NaOMe in methanol at 60° C. to contain approximately 57 weight % methyl 9-undecenoate, approximately 4 weight % dimethyl 9-octadecenedioate, and approximately 2 weight % methyl 9-octadecenoate (as determined by gc).

Example 12

By the general procedures described in example 1, approximately 7 kg of cross metathesis product was produced by reacting SBO with 3 mol 1-butene/mol SBO double bond using 43 mg C827 catalyst/kg SBO, following catalyst removal with THMP. An initial 2.09 kg portion of the metathesis product was hydrogenated at 136° C. and 400 psig $H_2$ until hydrogen uptake ceased in a one gallon batch autoclave using 105 g of Johnson-Matthey A-7000 Sponge Metal™ catalyst. The resulting mixture was filtered warm (22-55° C.), yielding 1.40 kg filtrate and 350 g of a mixture consisting of the catalyst and the hydrogenated product. The entirety of the catalyst-containing mixture was returned to the one gallon reactor along with a second 2.18 kg portion of the metathesis product and a second hydrogenation reaction was similarly carried out until hydrogen uptake ceased. The catalyst was allowed to settle and the majority of the organic product was decanted and filtered, yielding 1.99 kg filtrate and 380 g catalyst-hydrogenated product mixture. The remaining approximately 3 kg of metathesis product was hydrogenated in two additional batch reactions that in like manner were carried out using the catalyst from the previous reaction, yielding 1.65 kg and 1.28 kg of hydrogenated product, respectively. The total weight of hydrogenated product that was isolated after filtration was 6.32 kg. Aliquots of the hydrogenated product were found by gas chromatographic analysis to contain approximately 30 weight % $C_8$-$C_{18}$ n-paraffins and approximately 70 weight % triglycerides. The relative distribution of the $C_8$-$C_{18}$ n-paraffins contained in the hydrogenated product compares well with the calculated distribution of olefins by carbon number: observed (calculated) 2.3 (0.6) weight % $C_8$, 35.6 (36.2) weight % $C_9$, 30.0 (27.6) weight % $C_{10}$, 0.6 (0.1) weight % $C_{11}$, 22.2 (23.6) weight % $C_{12}$, 3.4 (3.7) weight % $C_{13}$, 0.1 (0.0) weight % $C_{14}$, 4.4 (6.3) weight % $C_{15}$, 0.4 (0.4) weight % $C_{16}$, 0.1 (0.0) weight % $C_{17}$, and 1.0 (1.6) weight % $C_{18}$.

The paraffin components were separated by wiped film evaporation from a 4.84 kg aliquot of the hydrogenated paraffin/triglyceride product. An initial wiped film evaporation was carried out at 75° C., 100 torr, 300 rpm, and condensation temperature of 15° C. using a feed rate of 300 g/h and yielded a condensate that was subjected to a second wiped film evaporation at 125° C., 90 torr, 300 rpm, and condensation temperature of 10° C. to remove the lighter alkanes. The resultant residual liquid was found by gas chromatography to contain the following distribution of n-alkanes: 17.5 weight % $C_7$, 1.7 weight % $C_8$, 31.0 weight % $C_9$, 28.3 weight % $C_{10}$, 0.6 weight % $C_{11}$, 17.4 weight % $C_{12}$, 2.1 weight % $C_{13}$, 0.1 weight % $C_{14}$, 1.2 weight % $C_{15}$, 0.1 weight % $C_{16}$, 0.0 weight $C_{17}$, and 0.1 weight % $C_{18}$. The material was found to have a heat of combustion of 43.86 MJ/kg (ASTM D3338), less than 1 mg/kg sulfur (ASTM D5453), density of 0.7247 (ASTM D4052), and a final boiling point of 232.3° C. (ASTM D86), indicating the majority of this material would be suitable as a blend stock in a fuel application such as diesel or jet fuel.

Example 13

An oligomerization reaction of 1-olefin/1,4-diene (92 wt % 1-decene, 4.5 wt % 1,4-decadiene, 2 wt % 1,4-undecadiene) that was produced from the cross metathesis of palm oil with 1-octene was performed on a 550 g scale using 1.1 mol % ethyl aluminum dichloride (1M solution in hexane)/1.1 mol % tert-butyl chloride for 3 hours at 10° C. The reaction mixture was quenched with water and 1M sodium hydroxide solution and stirred until it became colorless. Hexane (300 ml) was added and mixture was transferred to a separatory funnel. The organic layer was washed with water and brine, and then concentrated on a rotary evaporator to remove the hexane. The oligomeric mixture was devolatilized via short path vacuum distillation (100° C. and 5 Torr) and the product distribution was determined to be 97% mixture oligomers by GC/MS. The dynamic viscosity (Brookfield, #34 spindle, 100 rpm, 22° C.) of the sample is 540 cps. The kinematic viscosity for the sample at 40° C. is 232 cSt.

The aforementioned examples utilized the following analytical methods described below:

Volatile products were analyzed by gas chromatography and flame ionization detector (FID). Alkene analyses were performed using an Agilent 6890 instrument and the following conditions:

Column: Restek Rtx-5, 30 m×0.25 mm (ID)×0.25 μm film thickness
    Injector temperature: 250° C.
    Detector temperature: 280° C.
    Oven temperature: 35° C. starting temperature, 4 minute hold time, ramp rate 12° C./min to 260° C., 8 minute hold time
    Carrier gas: Helium
    Mean gas velocity: 31.3±3.5% cm/sec (calcula,ed)
    Split ratio: ~50:1

The products were characterized by comparing peaks with known standards, in conjunction with supporting data from mass spectrum analysis (GCMS-Agilent 5973N). GCMS analysis was accomplished with a second Rtx-5, 30 m×0.25 mm (ID)×0.25 μm film thickness GC column, using the same method as above.

Alkane analyses were performed using an Agilent 6850 instrument and the following conditions:

Column: Restek Rtx-65, 30 m×0.32 mm (ID)×0.1 μm film thickness
    Injector temperature: 250° C.
    Detector temperature: 350° C.
    Oven temperature: 55° C. starting temperature, 5 minute hold time, ramp rate 20° C./min to 350° C., 10 minute hold time
    Carrier gas: Hydrogen
    Flow rate: 1.0 mL/min
    Split ratio: 40:1

The products were characterized by comparing peaks with known standards. Fatty acid methyl ester (FAME) analyses were performed using an Agilent 6850 instrument and the following conditions:

Column: J&W Scientific, DB-Wax, 30 m×0.32 mm (ID)× 0.5 μm film thickness
    Injector temperature: 250° C.
    Detector temperature: 300° C.
    Oven temperature: 70° C. starting temperature, 1 minute hold time, ramp rate 20° C./min to 180° C., ramp rate 3° C./min to 220° C., 10 minute hold time
    Carrier gas: Hydrogen
    Flow rate: 1.0 mL/min The examples above collectively demonstrate the major steps described in the process schemes, showing the production of olefins, paraffins, metathesized triglycerides, unsaturated fatty acid esters and acids, and diacid compounds from natural oils that are useful as chemicals, solvents and fuels blending stocks.

What is claimed is:

1. A method of refining a natural oil, comprising:
providing (a) a feedstock comprising natural oil glycerides and (b) low-molecular-weight alpha-olefins;
cross-metathesizing the natural oil glycerides with the low-molecular-weight alpha-olefins in a metathesis reactor in the presence of a metathesis catalyst to provide a metathesized product comprising alpha-olefins and metathesized glycerides;
separating at least a portion of the alpha-olefins of the metathesized product and at least a portion of the metathesized glycerides of the metathesized product, to provide a first stream comprising separated alpha-olefins and second stream comprising separated metathesized glycerides;
transesterifying the separated metathesized glycerides of the second stream in the presence of an alcohol to provide a transesterified product comprising glycerin and fatty acid esters having no glycerin backbone; and
recycling at least a portion of the separated alpha-olefins of the first stream to the metathesis reactor.

2. The method of claim 1, further comprising treating the feedstock, prior to cross-metathesizing the natural oil glycerides with the low-molecular-weight alpha-olefins, under conditions sufficient to diminish catalyst poisons in the feedstock.

3. The method of claim 2, wherein the treating comprises chemically treating the feedstock through a chemical reaction with a reducing agent or a cation-inorganic base composition to diminish the catalyst poisons, wherein the reducing agent is selected from the group consisting of bisulfites, borohydrides, phosphines, thiosulfates, and phosphates.

4. The method of claim 2, wherein the treating comprises heating the feedstock to a temperature greater than 150° C. in the absence of oxygen for a time sufficient to diminish the catalyst poisons.

5. The method of claim 1, further comprising separating the metathesis catalyst from the alpha-olefins and the metathesized glycerides with a water soluble phosphine reagent.

6. The method of claim 1, wherein the metathesis catalyst is dissolved in a solvent.

7. The method of claim 6, wherein the solvent is toluene.

8. The method of claim 1, further comprising oligomerizing the separated alpha-olefins of the first stream to provide at least one of: poly-alpha-olefins, poly-internal-olefins, mineral oil replacements, or biodiesel.

9. The method of claim 1, further comprising:
separating the glycerin from the transesterified product through a liquid-liquid separation;
after separating the glycerin, washing the transesterified product; and
after the washing, drying the transesterified product.

10. The method of claim 1, further comprising distilling the transesterified product to separate a specialty chemical, wherein the specialty chemical is a 9-decenoic acid ester, a 9-dodecenoic acid ester, or any combinations thereof.

11. The method of claim 10, further comprising hydrolyzing the specialty chemical to provide 9-decenoic acid, 9-dodecenonic acid, or any combinations thereof.

12. The method of claim 1, further comprising reacting the fatty acid esters of the transesterified product with themselves to provide a dibasic ester.

13. The method of claim 1, wherein the low-molecular-weight alpha-olefins comprise ethylene, propylene, 1-butene, or any combinations thereof.

14. The method of claim 1, further comprising hydrolyzing the fatty acid esters, thereby providing fatty acids.

15. The method of claim 1, wherein the natural oil glycerides comprise a natural oil triglyceride selected from the group consisting of vegetable oils, algae oils, animal fats, and combinations thereof.

16. The method of claim 1, wherein the natural oil glycerides comprise a vegetable oil selected from the group consisting of: canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, pennycress oil, camelina oil, castor oil, and combinations thereof.

17. The method of claim 1, wherein the natural oil glycerides comprise a vegetable oil selected from the group consisting of: soybean oil, palm oil, canola oil, and combinations thereof.

18. The method of claim 1, wherein the alcohol is methanol or ethanol.

19. The method of claim 1, wherein the low-molecular-weight alpha-olefins comprise ethylene.

20. The method of claim 1, wherein the low-molecular-weight alpha-olefins comprise 1-butene.

21. The method of claim 1, wherein the portion of the separated alpha-olefins of the first stream recycled to the metathesis reactor comprises C2-C6 recycle alpha-olefins.

22. The method of claim 1, wherein the portion of the separated alpha-olefins of the first stream recycled to the metathesis reactor comprises C3-C5 recycle alpha-olefins.

23. The method of claim 1, wherein the portion of the separated alpha-olefins of the first stream recycled to the metathesis reactor comprises C3-C8 recycle alpha-olefins.

24. The method of claim 8, wherein the oligomerizing provides an olefin byproduct composition, and wherein the portion of the separated alpha-olefins of the first stream recycled to the metathesis reactor comprises the olefin byproduct composition.

25. The method of claim 1, further comprising partially hydrogenating the portion of the separated alpha-olefins of the first stream recycled to the metathesis reactor.

26. A method of refining a natural oil comprising:
providing (a) a feedstock comprising natural oil glycerides and (b) low-molecular-weight alpha-olefins having 4 to 10 carbon atoms;
cross-metathesizing the natural oil glycerides with the low-molecular-weight alpha-olefins in a metathesis reactor in the presence of a metathesis catalyst to provide a metathesized product comprising alpha-olefins and metathesized glycerides;
separating at least a portion of the alpha-olefins of the metathesized product and at least a portion of the metathesized glycerides of the metathesized product, to provide a first stream comprising separated alpha-olefins and a second stream comprising separated metathesized glycerides;
transesterifying the separated metathesized glycerides of the second stream in the presence of an alcohol to provide a transesterified product comprising glycerin and fatty acid esters having no glycerin backbone; and
recycling at least a portion of the separated alpha-olefins of the first stream to the metathesis reactor, wherein the portion of the separated alpha-olefins of the first stream recycled to the metathesis reactor comprises C2-C6 recycle alpha-olefins.

27. A method of refining a natural oil comprising:
providing (a) a feedstock comprising natural oil glycerides and (b) low-molecular-weight alpha-olefins comprising ethylene;
cross-metathesizing the natural oil glycerides with the low-molecular-weight alpha-olefins in a metathesis reactor in the presence of a metathesis catalyst to provide a metathesized product comprising alpha-olefins and metathesized glycerides;
separating at least a portion of the alpha-olefins of the metathesized product and at least a portion of the metathesized glycerides of the metathesized product, to provide a first stream comprising separated alpha-olefins and a second stream comprising separated metathesized glycerides;
transesterifying the separated metathesized glycerides of the second stream in the presence of an alcohol to provide a transesterified product comprising glycerin and fatty acid esters having no glycerin backbone; and
recycling at least a portion of the separated alpha-olefins of the first stream to the metathesis reactor, wherein the portion of the separated alpha-olefins of the first stream recycled to the metathesis reactor comprises C2-C6 recycle alpha-olefins.

* * * * *